(12) United States Patent
Ren et al.

(10) Patent No.: US 8,530,680 B2
(45) Date of Patent: Sep. 10, 2013

(54) SYSTEM AND METHOD FOR CONTROLLING GROWTH OF MICROORGANISMS WITH BROMINATED FURANONES

(75) Inventors: Dacheng Ren, Syracuse, NY (US); Yan Yeung Luk, Jamesville, NY (US)

(73) Assignee: Syracuse University, Syracuse, NY (US)

( * ) Notice: Subject to any disclaimer, the term of this patent is extended or adjusted under 35 U.S.C. 154(b) by 0 days.

(21) Appl. No.: 13/529,411

(22) Filed: Jun. 21, 2012

(65) Prior Publication Data
US 2012/0264950 A1  Oct. 18, 2012

Related U.S. Application Data

(62) Division of application No. 12/618,210, filed on Nov. 13, 2009.
(60) Provisional application No. 61/114,265, filed on Nov. 13, 2008.

(51) Int. Cl.
*C07D 307/48* (2006.01)
*A01N 43/08* (2006.01)

(52) U.S. Cl.
USPC ............................ 549/479; 514/473

(58) Field of Classification Search
USPC ............................ 549/479; 514/473
See application file for complete search history.

(56) References Cited

FOREIGN PATENT DOCUMENTS
WO 02-00639 1/2002
WO 02-47681 6/2002

OTHER PUBLICATIONS

Haval, Synthesis (2007), (14), 2198-2202.*
Han et al. Bioorganic & Medicinal Chemistry Letters (2008), 18(3), 1006-1010.*
Y. Han et al., Bioorganic & Medicinal Chemistry Letters, Dec. 31, 2007, vol. 18, pp. 1006-1010.
S. Al-Bataineh et al. Surface and Interface analysis, 2006, vol. 38 pp. 1512-1518.

* cited by examiner

*Primary Examiner* — Nizal Chandrakumar
(74) *Attorney, Agent, or Firm* — Frederick J. M. Price; Bond Schoeneck & King

(57) ABSTRACT

A method for inhibiting the growth of a microorganism using an effective amount of one or more of the following synthetic brominated furanones: (i) 4-bromo-5Z-(bromomethylene)-3-methylfuran-2-one; (ii) 3-(dibromomethyl)-5-(dibromomethylene)furan-2-one; (iii) 3-(bromomethyl)-5-(dibromomethylene)furan-2-one; (iv) 4-bromo-3-(bromomethyl)-5Z-(bromomethylene)furan-2-one; or (v) 4-bromo-5-(dibromomethyl)-3-methylfuran-2(5H)-one. The brominated furanones inhibit the growth of both fungi and bacteria, including the fungal species *Candida albicans, Gloeophyllum trabeum, Chaetomium globosum*, and *Trametes versicolor* and the bacterial species *Pseudomonas aeruginosa*. The brominated furanones can be used topically or internally to treat human infections, and can be used to treat other objects, such as wood building supplies, to prevent fungal rot.

5 Claims, 14 Drawing Sheets

BF1          BF9          BF13

BF15          NF1          NF2

NF3

BF8

BF10

BF11

BF12

BF14

SYSTEM AND METHOD FOR CONTROLLING GROWTH OF MICROORGANISMS WITH BROMINATED FURANONES

CROSS-REFERENCE TO RELATED APPLICATIONS

The present application is a divisional application of U.S. patent application Ser. No. 12/618,210, filed Nov. 13, 2009, which claims priority to U.S. Provisional Application No. 61/114,265, filed Nov. 13, 2008, each of which is expressly incorporated by reference herein.

STATEMENT REGARDING FEDERALLY SPONSORED RESEARCH OR DEVELOPMENT

This invention was made with government support under Grant No. X-83232501-0, which was awarded by the U.S. Environmental Protection Agency (EPA). The government has certain rights in the invention.

BACKGROUND OF THE INVENTION

1. Field of the Invention

The present invention relates to antimicrobials, and, more particularly, to antimicrobials for the control of *Candida albicans*, wood decay fungi, and *Pseudomonas aeruginosa*.

2. Description of the Related Art

Microorganisms are among the most diverse groupings of organisms on earth and include viruses, bacteria, and fungi. Microorganisms are ubiquitous and can be found in almost every habitat. In addition to the many natural processes of microbes, these microscopic organisms have been exploited by humans for a wide variety of beneficial uses. Despite these beneficial uses, many types of microorganisms are pathogenic to humans and cause increasing numbers of deaths annually.

Fungi, for example, are a large group of eukaryotic organisms that include yeasts, molds, and mushrooms. Fungi can be found in almost every habitat including aquatic, high salt, and high radiation environments. Although approximately 100,000 species of fungi have been identified to date, it is estimated that there are as many as 1.5 million more species yet to be characterized.

Although many species of fungi have beneficial uses including as a direct or indirect food source, an agent for the production of antibiotics, the subject of basic scientific research, and a biological agent to control other unwanted species, fungi also cause millions of dollars in damage every year. Several species of fungi are pathogens that cause serious and even deadly infections in humans, while other species destroy food sources or stores. Still other species have the capacity to digest man-made materials, thereby causing serious structural damage to buildings.

In humans, the fungi Candida is the primary fungal pathogen as well as the fourth most common class of microbes causing bloodstream infections. In particular, the *Candida albicans* ("*C. albicans*") yeast species represents 53.2 percent of *Candida* infections in the U.S. According to the Surveillance and Control of Pathogens of Epidemiologic Importance surveillance system of nosocomial bloodstream infections in U.S. hospitals, the mortality rate associated with nosocomial candidemia is 40 percent. In addition, yeast infections present a threat to immunocompromised HIV patients, since 60 percent of this population carries *C. albicans*. Despite the serious problems associated with fungal infections, there are only four classes of antifungal agents available for treatment, represented by azoles, polyenes, pyrimidines, and echinocandins. In general, these antifungal agents cause growth inhibition or cell death primarily by affecting the cell wall or membrane. The azole antifungals, such as fluconazole, are the most widely used antifungal drugs; they inhibit ergosterol synthesis in fungi and consequently cause the accumulation of toxic intermediates. Polyenes kill fungi by forming a channel through the membrane which leads to the leakage of intracellular components. The pyrimidines interfere with RNA synthesis and DNA replication in fungi. Echinocandins are a new class of antifungal drugs compared to the other three classes; they target the 1,3-β glucan synthase involved in the synthesis of cell wall components.

Although these antifungal agents exhibit a remarkable ability to combat fungal infections, fungal drug resistance has developed rapidly in the last two decades. One recent study has shown that 33 percent of late-stage AIDS patients carried drug-resistant *C. albicans* strains. Multiple factors contribute to *C. albicans* drug resistance, including the extrusion of toxic compounds through efflux pumps, the reduction of the permeability of membrane to drug molecules, the modification of drug targets, titration of the drug by the overexpression of drug-binding proteins, the degradation or modification of drug molecules, and substitution of the enzymes involved in the target pathway. For example, the ATP-binding cassette (ABC) transporters CDR1/CDR2 and the major facilitator MDR1 promote resistance by extruding drugs from the intracellular space. Besides the activation of efflux pumps among azole-resistant strains, mutations in ERG11 (encoding the azole target-14α-lanosterol demethylase) have been found to significantly reduce the affinity of drug molecules to their target proteins. In addition to the adaptive strategies exhibited by individual cells, *C. albicans* can also develop resistance by forming multicellular sessile communities known as biofilms on solid surfaces. Several studies have suggested that *C. albicans* biofilms are up to 1,000 times more resistant than their planktonic counterparts to antimicrobials such as fluconazole. These adaptive mechanisms have resulted in a significant increase in the number and severity of multidrug-resistant fungal infections and has exacerbated the demand for new antifungal drugs.

In addition to causing potentially deadly infections in humans, fungal growth can cause serious financial loss. Growth of fungi on lumber, for example, can result in costly structural damage, loss of building materials, and detrimental effects on indoor air quality. Wood damage by fungal growth can occur at several stages. Species can populate live trees, grow during transport and storage of cut timber, or populate finished structural elements. Rot caused by fungi—including both white rot and brown rot—results from the degradation of lignin and cellulose, the two components of wood. Three fungal organisms, *Gloeophyllum trabeum*, *Chaetomium globosum*, and *Trametes versicolor*, have been identified as the most serious offending species. The growth of fungi on indoor, outdoor, and stored building materials can result in significant costs to suppliers and home owners. Additionally, indoor growth of fungi can result in the release of toxins, leading to an unfavorable detrimental impact on the air quality of homes and offices.

Various techniques have been employed to prevent fungal growth in building materials. For example, wood is commonly treated with preserving chemicals such as zinc borate, flavanoids, and dimethyloldihydroxyethyleneurea. Wood is also treated with heat, pressure, and drying techniques to enhance decomposition resistance. However, the disposal of treated wood and general leaching of preservatives has caused serious environmental concerns. Additionally, heat and pressure methods used to prevent fungal growth may reduce the strength properties of some woods. As a result, there is still a need for antifungal treatment methods that are innocuous to the environment and will not affect the strength of building materials.

Since recent studies have shown that brominated furanones, produced as secondary metabolites by the marine red macro alga *Delisea pulchra*, have remarkable activities against the colonization of both prokaryotes and eukaryotes, they are promising reagents for fungal control. Several natural and synthetic furanones have been shown to control a variety of microbial phenotypes such as the growth of Gram-positive bacteria and multicellular behaviors of Gram-negative bacteria. For example, the natural furanone (5Z)-4-bromo-5-(bromomethylene)-3-butyl-2(5H)-furanone has been found to repress genes associated with chemotaxis, motility and flagellar synthesis in *E. coli*. This furanone has also been shown to have an inhibitory effect on the growth *Bacillus subtilis* and was found to induce genes associated with stress responses, fatty acid biosynthesis, lichenan degradation, transport, and metabolism in that organism. However, the inhibitory effects of many natural and synthetic brominated furanones on *C. albicans* or wood decay fungi have not yet been studied.

Bacterial infections also present serious problems to humans. In the U.S. alone, the treatment of nosocomial infections costs approximately USD$ 11 billion annually. Roughly half of these infections are related to medical devices that are implanted in patients for different lengths of duration. Device-associated infections are chronic with considerable morbidity and mortality. According to the Centers for Disease Control and Prevention, there are more than one million such cases annually in the U.S., which result in more than 45,000 deaths. It is well documented that the microbes causing device-associated infections are attached to surfaces and grow in biofilms, which are highly hydrated structures comprised of a polysaccharide matrix secreted by the bound microbes. Biofilm cells are up to 1000 times more tolerant to antimicrobials and disinfectants compared to their free-swimming counterparts. As a result, antibiotics can only eliminate planktonic cells and the symptoms reoccur upon the release of cells from biofilms.

Biofilms cause a wide range of problems for environment, industry, and public health-related issues. Consequences of biofilm formation include infections from medical devices such as intravenous catheters, joint prostheses, cardiac pacemakers, prosthetic heart valves, peritoneal dialysis catheters and cerebrospinal fluid shunts, as well as billions of dollars worth of damage in industry due to increased corrosion of metallic equipment. Thus, controlling biofilm formation is critically important for a broad range of concerns for both medical and industrial communities.

With the important roles that biofilms play in device-associated infractions and the unsatisfactory efficacy of antibiotics in treating such infections, it is important to develop new methods to control biofilm formation. Previous discoveries have shown that brominated furanones exhibit activity against the colonization of bacteria, but there is a continuing need to discover and develop brominated furanones that are effective against biofilm formation.

BRIEF SUMMARY OF THE INVENTION

It is therefore a principal object and advantage of the present invention to provide an antimicrobial agent.

It is another object and advantage of the present invention to provide an antifungal agent that may be used to treat and/or prevent yeast infection.

It is another object and advantage of the present invention to provide an antifungal agent that may be used to treat or prevent *Candida albicans* infection.

It is an additional object and advantage of the present invention to provide an antifungal agent that may be used to treat or prevent the growth of wood fungi.

It is yet another object and advantage of the present invention to provide an antifungal agent that may be used to treat or prevent the growth of Gloeophyllum trabeum, Chaetomium globosum, of *Trametes versicolor*.

It is a further object and advantage of the present invention to provide an antibacterial agent.

It is an additional object and advantage of the present invention to provide an antibacterial agent to treat or prevent the growth of *Pseudomonas aeruginosa*.

It is yet another object and advantage of the present invention to provide a method for the efficient synthesis of brominated furanones.

In accordance with the foregoing objects and advantages, the present invention utilizes the antifungal activity of natural and synthetic furanones. In particular, the invention provides the following synthetically produced brominated furanones: (i) 4-bromo-5Z-(bromomethylene)-3-methylfuran-2-one ("BF8"); (ii) 3-(dibromomethyl)-5-(dibromomethylene)furan-2-one ("BF10"); (iii) 3-(bromomethyl)-5-(dibromomethylene)furan-2-one ("BF11"); (iv) 4-bromo-3-(bromomethyl)-5Z-(bromomethylene)furan-2-one ("BF12"); (v) 4-bromo-5-(dibromomethyl)-3-methylfuran-2(5H)-one ("BF14").

Another embodiment of the present invention is a method for efficient synthesis of one or more synthetically produced brominated furanones using α-methyllevulic acid as a precursor.

A further embodiment of the present invention provides a method for inhibiting the growth of a microorganism, the method comprising treating the microorganism with an effective amount of one or more synthetically produced brominated furanone selected from the group consisting of: (i) 4-bromo-5Z-(bromomethylene)-3-methylfuran-2-one ("BF8"); (ii) 3-(dibromomethyl)-5-(dibromomethylene)furan-2-one ("BF10"); (iii) 3-(bromomethyl)-5-(dibromomethylene)furan-2-one ("BF11"); (iv) 4-bromo-3-(bromomethyl)-5Z-(bromomethylene)furan-2-one ("BF12"); (v) 4-bromo-5-(dibromomethyl)-3-methylfuran-2(5H)-one ("BF14").

Another embodiment of the present invention provides a method for inhibiting the growth of a fungi, the method comprising treating the fungi with an effective amount of one or more synthetically produced brominated furanone selected from the group consisting of: (i) 4-bromo-5Z-(bromomethylene)-3-methylfuran-2-one ("BF8"); (ii) 3-(dibromomethyl)-5-(dibromomethylene)furan-2-one ("BF10"); (iii) 3-(bromomethyl)-5-(dibromomethylene)furan-2-one ("BF11"); (iv) 4-bromo-3-(bromomethyl)-5Z-(bromomethylene)furan-2-one ("BF12"); (v) 4-bromo-5-(dibromomethyl)-3-methylfuran-2(5H)-one ("BF14"); wherein the fungi is selected from the group consisting of *Candida albicans, Gloeophyllum trabeum, Chaetomium globosum,* and *Trametes versicolor*.

Yet another embodiment of the present invention provides a method for inhibiting the growth of a bacterium, the method comprising treating the bacterium with an effective amount of one or more synthetically produced brominated furanone selected from the group consisting of: (i) 4-bromo-5Z-(bromomethylene)-3-methylfuran-2-one ("BF8"); (ii) 3-(dibromomethyl)-5-(dibromomethylene)furan-2-one ("BF10"); (iii) 3-(bromomethyl)-5-(dibromomethylene)furan-2-one ("BF11"); (iv) 4-bromo-3-(bromomethyl)-5Z-(bromomethylene)furan-2-one ("BF12"); (v) 4-bromo-5-(dibromomethyl)-3-methylfuran-2(5H)-one ("BF14"); wherein the bacterium is *Pseudomonas aeruginosa*.

A further embodiment of the present invention provides a method for treating wood, the method comprising treating the wood with an effective amount of one or more synthetically produced brominated furanone selected from the group consisting of: (i) 4-bromo-5Z-(bromomethylene)-3-methylfuran-2-one ("BF8"); (ii) 3-(dibromomethyl)-5-(dibromomethylene)furan-2-one ("BF10"); (iii) 3-(bromomethyl)-5-(dibromomethylene)furan-2-one ("BF11"); (iv) 4-bromo-3-(bromomethyl)-5Z-(bromomethylene)furan-2-one ("BF12"); (v) 4-bromo-5-(dibromomethyl)-3-methylfuran-2(5H)-one ("BF14").

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1A:
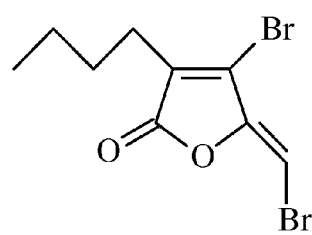
FIG. 1A is a schematic of the structures of the prior art furanones used in this study.
Figure 1A:
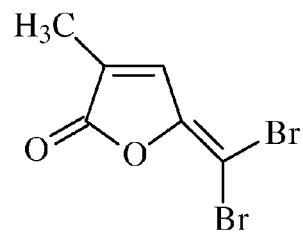
Figure 1A:
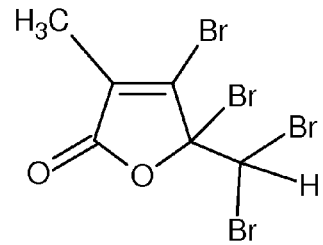
Figure 1A:
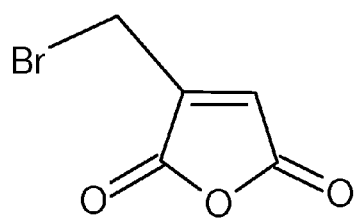
Figure 1A:
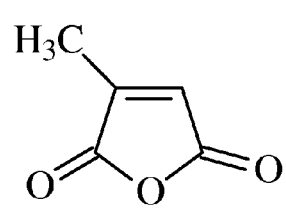
Figure 1A:
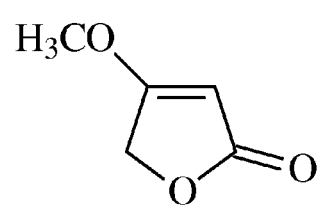
Figure 1A:
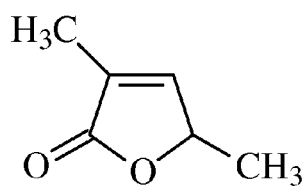
Figure 1B:
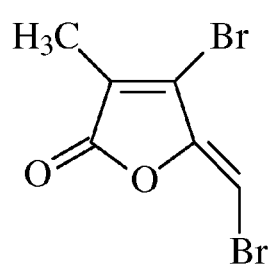
FIG. 1B is a schematic of the structures of the novel furanones used in this study.
Figure 1B:
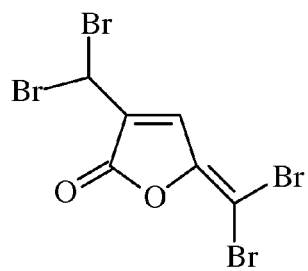
Figure 1B:
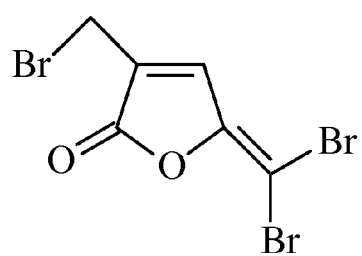
Figure 1B:
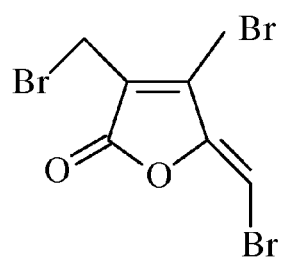
Figure 1B:
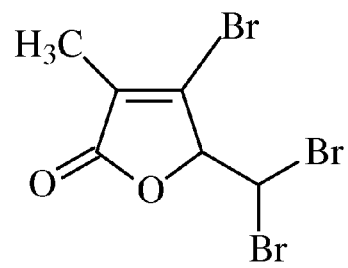

Referring now to the drawings, wherein like numerals refer to like parts throughout, the present invention comprises the use of furanones to inhibit the growth of microorganisms. In particular, the present invention comprises the use of novel brominated furanones to inhibit the growth of the fungal species *C. albicans, Gloeophyllum trabeum, Chaetomium globosum,* and *Trametes versicolor* and the bacterium *Pseudomonas aeruginosa*. Growth of these species can be inhibited by brominated furanones at concentrations ranging from 2.5 µg/mL to 20 µg/mL. Table 1 contains a list of the furanones currently examined. The structures of the novel brominated furanones from Table 1—BF8, BF10, BF11, BF12, and BF14—are shown in FIG. 1B. The structures of the remaining brominated and nonbrominated furanones are shown in FIG. 1A.

TABLE 1

| Abbreviation | Compound |
| --- | --- |
| BF1 | 4-bromo-5Z-(bromomethylene)-3-butylfuran-2-one |
| BF8 | 4-bromo-5Z-(bromomethylene)-3-methylfuran-2-one |
| BF9 | 5-(dibromomethylene)-3-methylfuran-2-one |
| BF10 | 3-(dibromomethyl)-5-(dibromomethylene)furan-2-one |
| BF11 | 3-(bromomethyl)-5-(dibromomethylene)furan-2-one |
| BF12 | 4-bromo-3-(bromomethyl)-5Z-(bromomethylene)furan-2-one |
| BF13 | 4-bromo-5-(dibromomethyl)-3-methylfuran-2(5Br)-one |
| BF14 | 4-bromo-5-(dibromomethyl)-3-methylfuran-2(5H)-one |
| BF15 | 3-(bromomethyl)-2,5-furandione |
| NF1 | Citraconic anhydride; IUPAC: 3-methyl-2,5-furandione |
| NF2 | 4-Methoxy-2(5H)-furanone; IUPAC: 4-methoxy-2(5H)-furanone |
| NF3 | 3,5-Dimethylfuran-2(5H)-one |

The antifungal activates of furanones found in this study, along with the inhibitory effects of furanones on the growth of Gram-positive bacteria and on the multicellular behaviors of Gram-negative bacteria, indicate that furanones could be developed as wide-spectrum antimicrobial agents for medical and industrial applications.

Example 1

Figure 2:
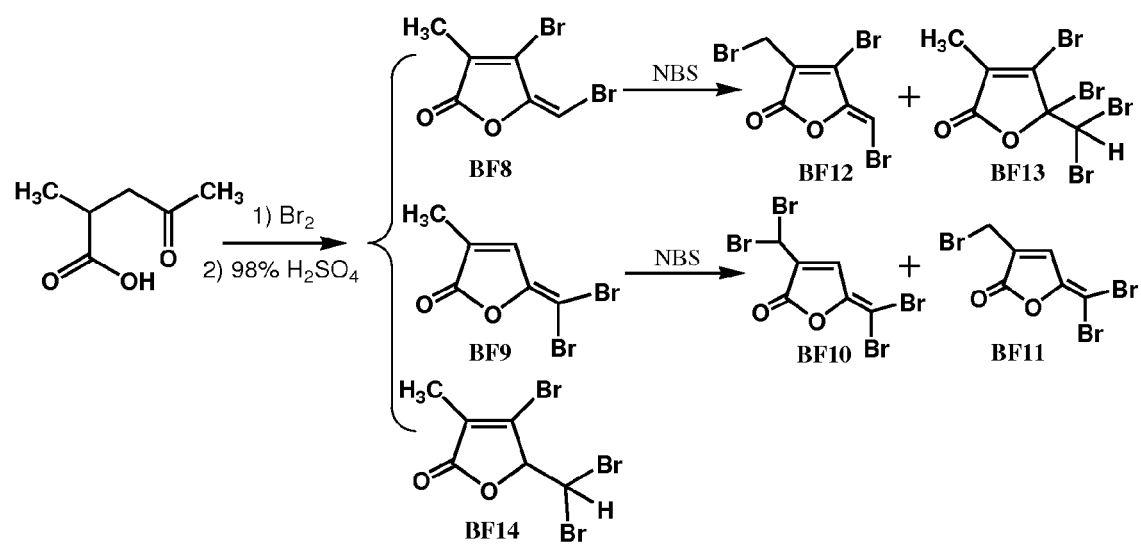
FIG. 2 is a schematic of the synthetic brominated furanone synthesis method according to one embodiment of the present invention.
Figure 3A:
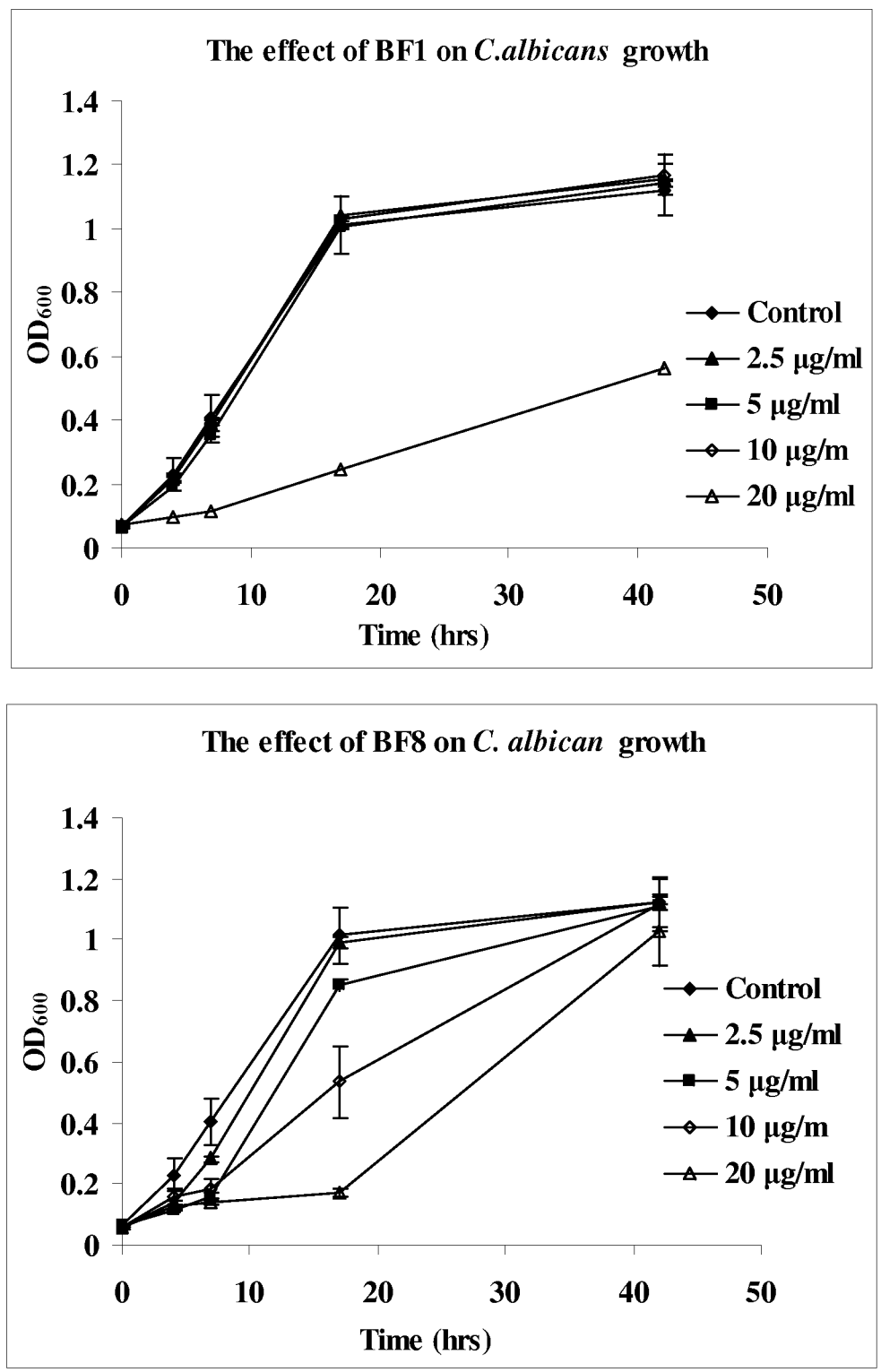
FIG. 3A is a graph of *Candida albicans* growth curves in the presence of brominated furanones BF1 and BF8 at a concentration of 0, 2.5, 5, 10, and 20 µg/mL.
Figure 3B:
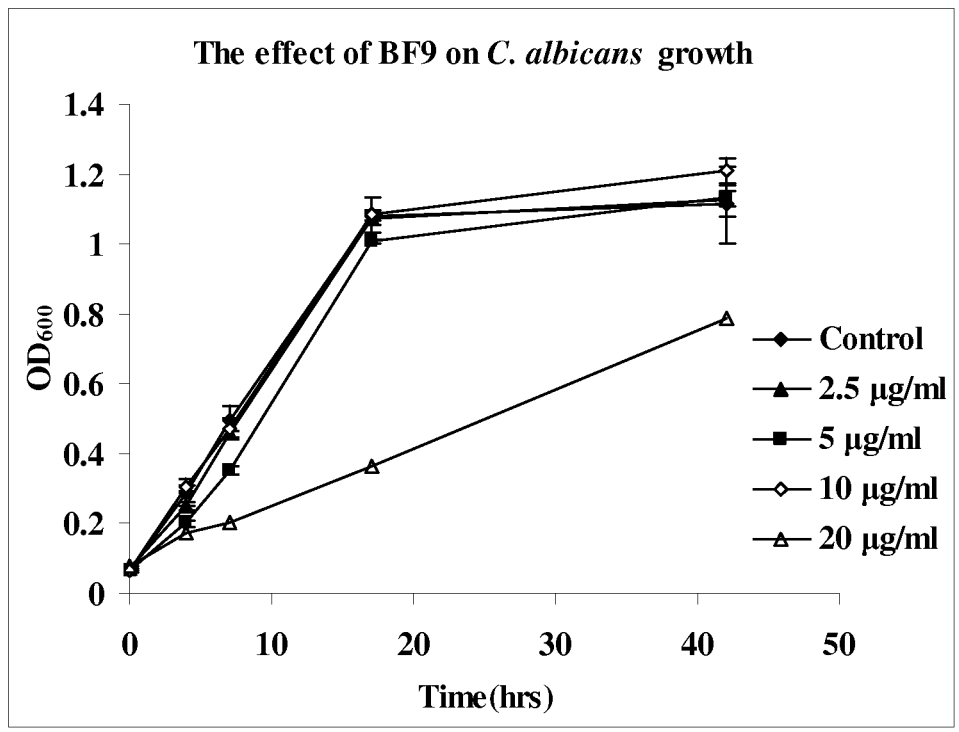
FIG. 3B is a graph of *Candida albicans* growth curves in the presence of the brominated furanones BF9 and BF10 at a concentration of 0, 2.5, 5, 10, and 20 µg/mL.
Figure 3B:
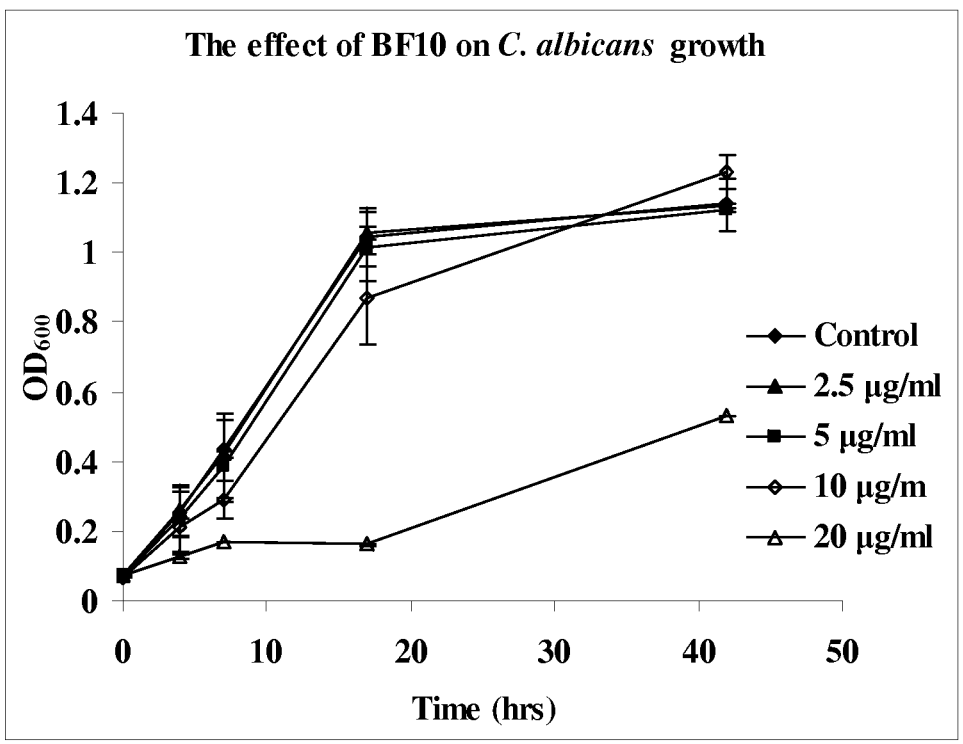
Figure 4A:
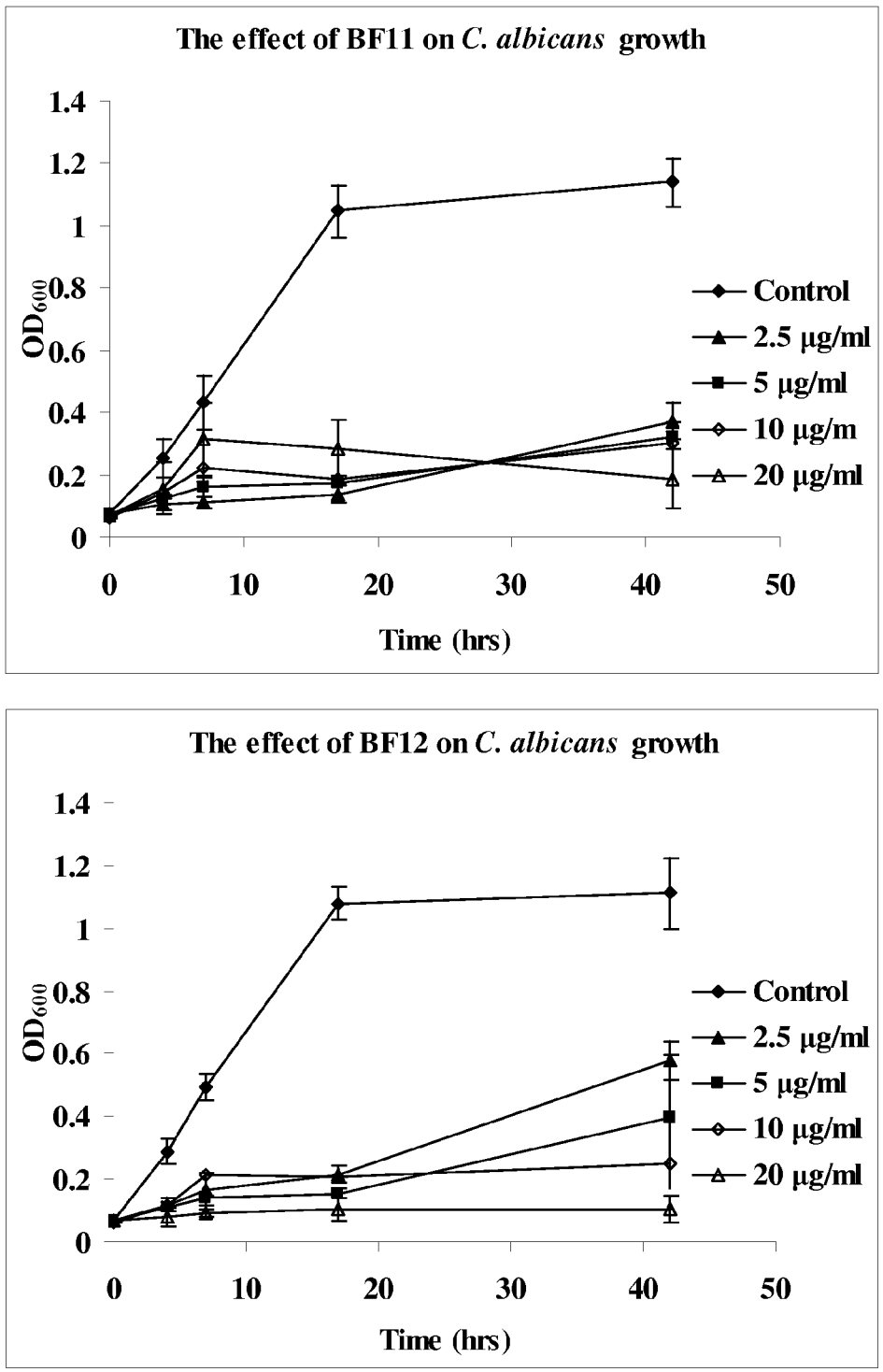
FIG. 4A is a graph of *Candida albicans* growth curves in the presence of the brominated furanones BF11 and BF12 at a concentration of 0, 2.5, 5, 10, and 20 µg/mL.
Figure 4B:
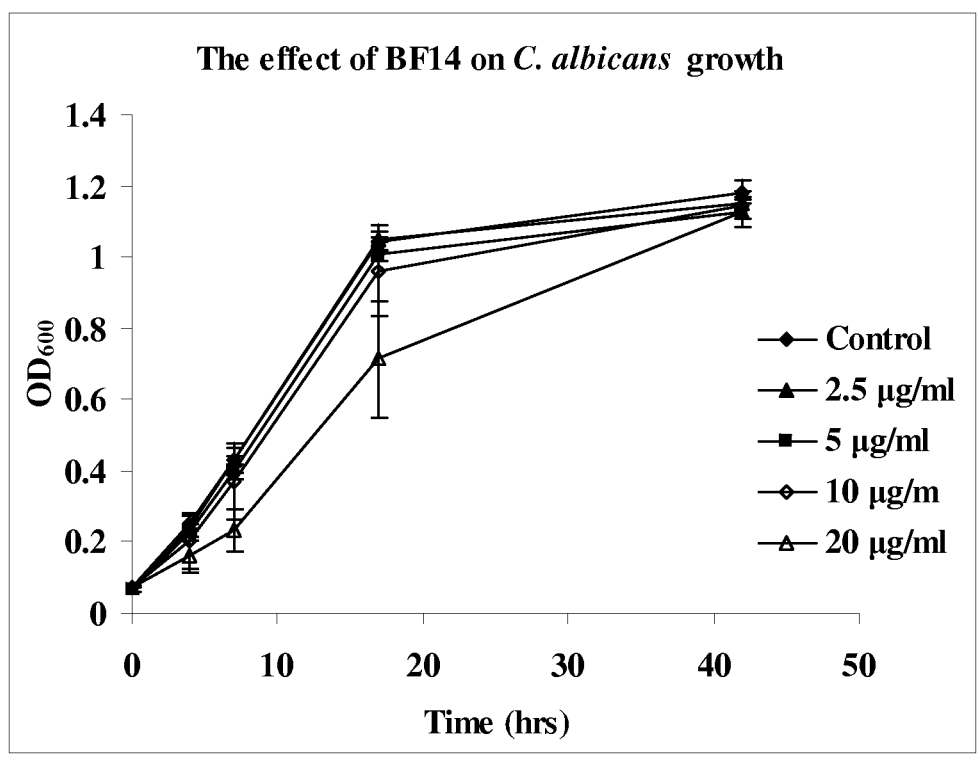
FIG. 4B is a graph of *Candida albicans* growth curves in the presence of the brominated furanone BF14 at a concentration of 0, 2.5, 5, 10, and 20 µg/mL.

The brominated furanones BF8, BF10, BF11, BF12, and BF14 were synthesized using a novel method, as shown in FIG. 2. First, brominated furanones BF8, BF9, and BF14 were synthesized via bromination of commercially available α-methyllevulic acid followed by oxidative ring closure under acidic condition. A Wohl-Ziegler bromination reaction was then used to obtain BF12 and BF13 from BF8 as well as BF10 and BF11 from BF9. In a preferred embodiment of the synthesis method, the brominated α-methyllevulic acid was treated with 98% $H_2SO_4$ to promote intramolecular cyclization, and the Wohl-Ziegler reaction used commercially available N-Bromosuccinimide ("NBS").

The synthetic molecules were separated and purified by column chromatography to obtain a purity of at least 95%, and all the molecules were characterized by proton and carbon-13 nuclear magnetic resonance spectroscopy as well as by high resolution mass spectroscopy.

Among other benefits, this novel method of synthesis employs starting materials and reagents—including alpha-methyllevulic acid and N-Bromosuccinimide—which can be easily and economically purchased from many chemical supply companies.

Example 2

To evaluate the effects of furanones on fungal growth, *C. albicans* was grown in a synthetic dextrose ("SD") medium supplemented with 0, 2.5, 5, 10, or 20 µg/mL of one of eight different brominated furanones and two nonbrominated furanones (BF1, BF8, BF9, BF11, BF12, BF14, NF1, NF2, or NF3).

The brominated furanones were synthesized as described in Example 1, while NF1 and NF2 were obtained from Sigma® (St. Louis, Mo.). NF3 was obtained by treating α-methyllevulic acid with phosphoric acid ($H_3PO_4$) at 140-150° C. All of the synthetic molecules were purified by column chromatography to obtain a purity of at least 95%. All molecules were characterized by proton and carbon 13 nuclear magnetic resonase (NMR) spectroscopy and high resolution mass spectroscopy (HRMS).

The *Candida albicans* strain SC5341 used in this study was provided by Dr. Sean Palecek from the University of Wisconsin-Madison. *C. albicans* was routinely grown overnight at 30° C. and shaken at 200 rpm in a SD medium containing 0.67% (wt/vol) yeast nitrogen base without amino acids and 2% (wt/vol) dextrose, which was buffered with 0.165 M morpholinepropanesulfonic acid (MOPS, Sigma), and pH-adjusted to 7.0 with solid NaOH. The overnight culture was then sub-cultured in 25 mL of fresh SD medium to an initial optical density at 600 nm ($OD_{600}$) of 0.005 and grown till the $OD_{600}$ reached 1.0. The $OD_{600}$ values were measured using a Spectronic GENESYS 5 UV-Vis spectrophotometer (Thermo Fisher Scientific®, Waltham, Mass.). This culture was used to inoculate sterile 96-well plates (Costar® No. 9017, Corning®, Corning, N.Y.) containing SD medium supplemented with furanones at different concentrations (0, 2.5, 5, 10, 20 µg/mL) to an $OD_{600}$ of 0.06 in at least duplicates. The BF1, 8, 9, 11, 12, 14 and NF1-3 compounds were dissolved in ethanol at a concentration of 20 mg/mL. The BF10 compound was dissolved in methanol at a concentration of 20 mg/mL. The amounts of methanol and ethanol were adjusted to be the same for each sample to eliminate the effects of solvents. The samples were then incubated at 30° C. with shaking at 200 rpm, and the $OD_{600}$ in each well was measured at 0, 4, 7, 17, and 42 hours after inoculation, using an ELx808™ Absorbance Microplate Reader (BioTek Instruments® Inc., Winooski, Vt.).

FIGS. 3A, 3B, 4A, and 4B show the growth curves of *C. albicans* in the presence and absence of the six BF compounds. BF11 and BF12 exhibited the strongest inhibitory effects, causing significant reduction of cell growth. At 17 hours after inoculation, the growth yield of the samples with 2.5 µg/mL of either furanone was less than 20% of that without furanone. BF11 and BF12 also significantly inhibit the growth of *E. coli* (results not shown). These findings suggest that the monosubstituted bromides on an exocyclic methyl group can lead to high toxicity to microbes. BF1, BF9, BF10, and BF 14 started to show significant growth inhibition at a concentration of 20 µg/mL. At 7 hours after inoculation, the growth yields of the samples with furanone were less than 60% of those without furanone. In comparison, BF8 inhibited cell growth at concentrations as low as 5 µg/mL.

Figure 5A:
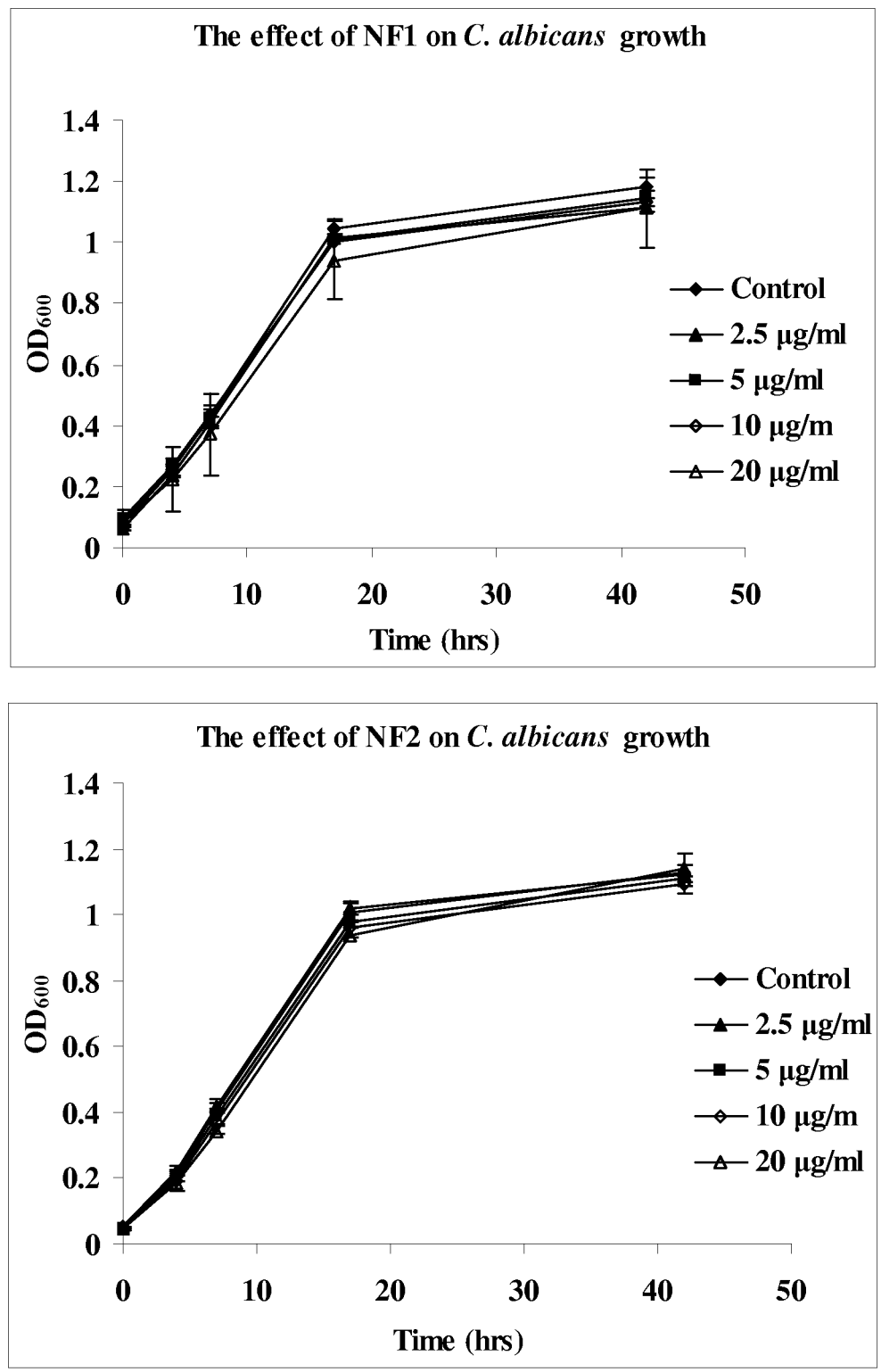
FIG. 5A is a graph of the *Candida albicans* growth curves in the present of the non-brominated furanones NF1 and NF2 at a concentration of 0, 2.5, 5, 10, and 20 µg/mL.
Figure 5B:
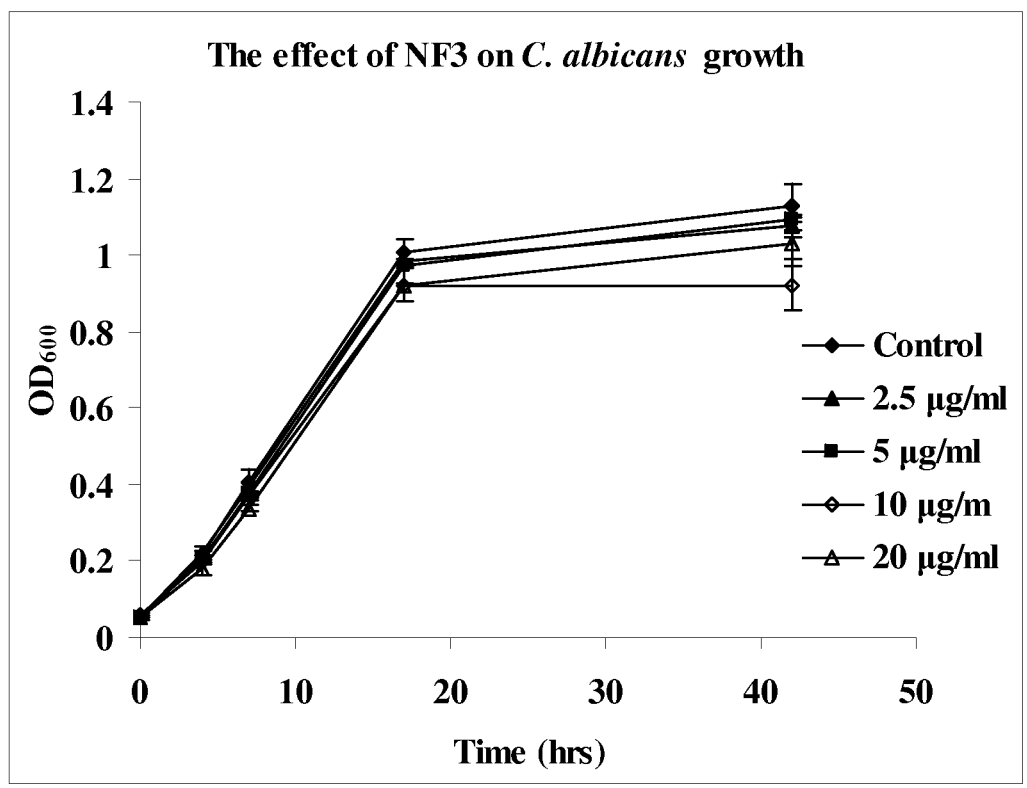
FIG. 5B is a graph of the *Candida albicans* growth curves in the presence of the non-brominated furanone NF3 at a concentration of 0, 2.5, 5, 10, and 20 µg/mL.

FIGS. 5A and 5B shows the growth curves of *C. albicans* in the presence and absence of the three NF compounds. None of the NFs inhibited cell growth at concentrations up to 20 µg/mL, which suggests that the bromide group is required for growth inhibition. Examining the structures of BF8 and BF14, it can be seen that BF8 bears an exocyclic vinyl bromide conjugated with the carbonyl group, while BF14 does not, suggesting this bromide group is important for the inhibition of *C. albicans*. Interestingly, BF8 at 60 µg/mL also did not inhibit the growth of *E. coli* (results not shown). The monosubstituted bromides on an exocyclic methyl group, which presents only on BF11 and BF12, led to strong inhibition of *C. albicans* and *E. coli* growth. Considering that BF8 was active at 5 µg/mL, which is lower than 20 µg/mL (the lowest active concentration of BF14), the exocyclic vinyl bromide conjugated with the carbonyl group could be responsible for the growth inhibition by BF8 at low concentrations.

Example 3

To further examine the effect of brominated furanones on fungal growth and understand whether BFs are fungicidal agents to *C. albicans*, BF1 was used as the representative compound in a viability assay based on colony-forming unit ("CFU") counting. An overnight culture of *C. albicans* was sub-cultured in 100 mL of SD medium to an initial $OD_{600}$ of 0.005 and was grown for 24 hours. The cells were then harvested by centrifugation at 4,500 rpm for 5 minutes at room temperature and washed twice with 0.85% NaCl buffer. Then the cells were resuspended in 0.85% NaCl buffer and supplemented with 0, or 60 µg/mL BF1, BF8, BF9, BF10, BF11, BF12, or BF14 to an $OD_{600}$ of 2.0 using 17×100-mm polystyrene test tubes (Fisher Scientific). After incubation at 30° C. for 6 hours with shaking at 200 rpm, the treated cells were spread on Yeast Extract Peptone Dextrose (YPD) plates containing 20 g/L peptone, 10 g/L yeast extract, 20 g/L dextrose and 15 g/L agar. The colony-forming units (CFUs) on the plates were counted after 24 hours of incubation at 30° C. to evaluate the killing of *C. albicans* by furanones. Duplicate samples for each furanone were tested and five agar plates were counted for each sample.

Figure 6:
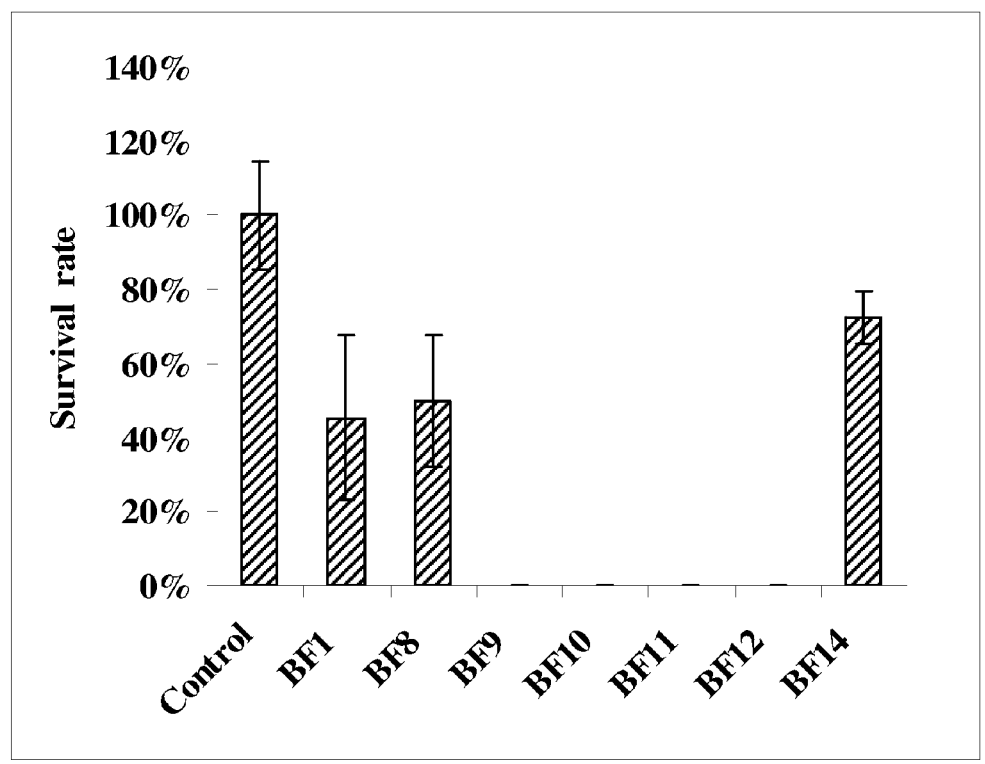
FIG. 6 is a graph of the fungicidal effects of brominated furanone BF1 on *C. albicans*.

FIG. 6 is graph representing the survival rate of *C. albicans* after exposure to 60 µg/mL BF1, BF8, BF9, BF10, BF11, BF12, or BF14 for 6 hours in 0.85% NaCl buffer. All BFs were found to reduce CFU significantly. For example, after treatment with 60 µg/mL of BF8 and BF10 for 6 hours in 0.85% NaCl buffer, the CFU of *C. albicans* was reduced by 50% and 100% respectively. This finding suggests that BFs are indeed fungicidal to *C. albicans*.

Example 4

The inhibitory effect of furanone on the growth of *Bacillus subtilis* have previously been explored by DNA microarrays. To further understand the mechanism of fungal growth inhibition mediated by brominated furanones, the gene expression pattern of *C. albicans* following treatment with 3 µg/mL BF1 was examined using DNA microarrays for the first time.

An overnight culture of *C. albicans* strain SC5341 grown in SD medium was sub-cultured in 25 mL of the same medium to an initial $OD_{600}$ of 0.005 and grown till the $OD_{600}$ was 1.0. The culture was diluted using fresh SD medium to a volume of 100 mL with an initial $OD_{600}$ of 0.6, and it was grown till the $OD_{600}$ reached 1.0, which took approximately 2 hours. Then the culture was split into two equal portions, with 3 µg/mL of BF1 added to the first one and the same amount of ethanol added to the second one to eliminate the effects of ethanol. The concentration of 3 µg/mL was chosen because it was shown to reduce the specific growth rate of *C. albicans* by approximately 50% after 3 hours of treatment in a shake flask (data not shown). Forty-five minutes after BF1 addition, the cells were harvested by centrifugation at 13,200 rpm at 4° C. for 30 sec and stored at −80° C. until RNA isolation. To lyse the cells, 1.5 mL of Trizol reagent (Invitrogen® Co., Carlsbad, Calif.) and 0.5 mL of 0.5 mm glass beads were added to the frozen tubes containing *C. albicans* cell pellets. The tubes were closed tightly and beaten for 30 sec at 4,800 oscillations/minute using a mini bead beater (Biospec Products Inc., Bartlesville, Okla.). The total RNA was extracted using Trizol reagent by following the manufacture's protocol. The extracted RNA was further cleaned up using an RNeasy mini-kit (QIAGEN® Inc., Valencia, Calif.), including on-column DNA digestion with RNase-free DNase I. The RNA yield was quantified by $OD_{260}$ reading, and the RNA integrity was checked, using agarose gel electrophoresis. The RNA samples were sent to the DNA MicroArray Lab at the Biotechnology Research Institute, National Research Council of Canada (Montreal, Canada) to further check the integrity and DNA microarray hybridization. RNA from a control sample and that from a furanone-treated sample were hybridized to each array. A total of four DNA microarrays were used and four biological replicates were tested. The data were analyzed using Genespring GX version 7.3 (Agilent Technologies®, Santa Clara Calif.). A gene was considered differentially expressed if it was induced/repressed more than 1.5-fold and had a t-test p-value less than 0.05. Gene functions were annotated by searching the *Candida* Genome Database at (www.candidagenome.org).

The microarray data indicate that BF1, at a sublethal concentration (3 µg/mL), led to a significant modulation ($P \leq 0.05$) of a total of 54 genes, including a number of genes involved in the stress response and small molecule transport. Among the 54 modulated genes, 33 genes were induced and 21 genes were repressed by at least 1.5-fold. Table 2 is a summary of the 33 genes induced by exposure to 3 µg/mL BF1. The largest group of genes being up-regulated was of unknown function (28%), followed by those involved in the stress response (25%), NADPH dehydrogenase activity (16%), the transport of small molecules (13%), cell cycling and DNA processing (6%), cell wall maintenance (3%), and other functions (9%).

TABLE 2

| Systematic Name | Standard Name | Induction expression ratio | Functions |
|---|---|---|---|
| Response to stress: | | | |
| orf19.3340 | SOD2 | 1.72 | manganese-superoxide dismutase |
| orf19.6059 | TTR2 | 1.80 | glutaredoxin |
| orf19.5059 | GCS1 | 1.96 | gamma-glutamylcysteine synthetase |
| orf19.2396 | IFR2 | 2.05 | alcohol dehydrogenase |
| orf19.3707 | YHB1 | 2.65 | flavohemoglobin; dihydropteridine reductase |
| orf19.2262 | — | 2.68 | probable quinone oxidoreductase |
| orf19.113 | CIP1 | 3.17 | cadmium-induced protein |
| orf19.5604 | MDR1 | 5.36 | benomyl/methotrexate resistance protein |
| orf19.2175 | — | 10.94 | oxidoreductase similar to mammalian Apoptosis Inducing Factor |
| NADPH dehydrogenase activity: | | | |
| orf19.3433 | OYE23 | 20.04 | NAPDH dehydrogenase (old yellow enzyme), isoform 2 |
| orf19.125 | EBP1 | 13.87 | NADH: flavin oxidoreductase (old yellow enzyme) |
| orf19.3131 | OYE32 | 12.89 | NADPH dehydrogenase |
| orf19.3234 | OYE22 | 4.00 | NADPH dehydrogenase |
| orf19.3443 | OYE2 | 3.30 | NAPDH dehydrogenase (old yellow enzyme) |
| Small molecule transport: | | | |
| orf19.1783 | YOR1 | 1.78 | oligomycin resistance ATP-dependent permease |

TABLE 2-continued

| Systematic Name | Standard Name | Induction expression ratio | Functions |
|---|---|---|---|
| orf19.4940 | HIP1 | 2.57 | histidine permease |
| orf19.23 | RTA3 | 5.01 | putative transporter or flippase transmembrane protein |
| orf19.5604 | MDR1 | 5.36 | benomyl/methotrexate resistance protein |
| Other functions: | | | |
| orf19.1421 | DAL3 | 1.58 | ureidoglycolate hydrolase |
| orf19.1167 | — | 1.65 | sulfonate dioxygenase |
| orf19.1237 | ARO9 | 1.87 | aromatic amino acid amino-transferase II |
| Cell cycling and DNA processing: | | | |
| orf19.5992 | WOR2 | 1.54 | Transcriptional regulator of white-opaque switching |
| orf19.2693 | | 3.97 | transcription corepressor |
| Cell wall maintenance: | | | |
| orf19.896 | CHK1 | 1.54 | histidine kinase osmosensor; two-component signal transducer |
| Unknown function: | | | |
| orf19.3139 | — | 8.82 | conserved hypothetical protein |
| orf19.1286 | — | 1.97 | hypothetical protein |
| orf19.93 | — | 1.53 | conserved hypothetical protein |
| orf19.2825 | DRE2 | 1.69 | conserved hypothetical protein |
| orf19.6275 | — | 1.94 | hypothetical protein |
| orf19.7531 | — | 2.53 | conserved hypothetical protein |
| orf19.7306 | — | 2.87 | conserved hypothetical protein |
| orf19.6869 | — | 4.21 | conserved hypothetical protein |
| orf19.320 | — | 14.98 | hypothetical protein |

Nine stress response genes were induced by BF1, as shown in Table 2. Among them, expression of orf19.2175 was recently found to be induced by nitric oxide, an antimicrobial compound produced by the innate immune system of mammals. According to basic local alignment search tool ("BLAST") (http://www.ncbi.nlm.nih.gov/BLAST/) search results, orf19.2175 shares 42% identities and 63% positives with AIF1 of *Saccharomyces cerevisiae* ("*S. cerevisiae*"). AIF1 is involved in NADH or NADPH oxidoreductase activity and could possibly have a function similar to that of the five other induced genes in the NADPH dehydrogenase group.

Besides orf19.2175, seven of the induced *C. albicans* genes (MDR1, SOD2, IFR2, CIP1, orf19.2262, YHB1, and TTR2) are involved in oxidative stress response. The first five are regulated via CAP1, a transcription factor participating in stress response and multidrug resistance. Interestingly, although 8 of the induced genes (OYE23, EBP1, OYE32, MDR1, SOD2, IFR2, CIP1, and orf19.2262) also respond to oxidative stress via CAP1, the expression level of CAP1 remained the same with and without BF1. In a previous study, CAP1 was found to be induced 10 mins and 30 mins after $H_2O_2$ treatment, but not at 50 mins. In addition, 76 out of 89 genes expressed differentially with $H_2O_2$ treatment showed CAP1-dependent expression. These data suggest that CAP1 is a transcription regulator for oxidative stress response genes, which was only induced at the early stage of stress exposure. Another stress response gene induced by BF1 called GCS1 or gamma-glutamylcysteine synthetase, is also induced by $H_2O_2$.

There were five genes with NADPH dehydrogenase activities (OYE23, EBP1, OYE32, OYE 22, and OYE2) highly induced by BF1 (in the range of 3.3 to 20 fold), as shown in Table 2. OYE23, EBP1 and OYE32 have been shown to be induced by nitric oxide or benomyl via CAP1, while OYE2 was only induced by nitric oxide. The induction of these genes by fungicidal BF1 further indicates that they are also involved in the C. albicans stress response.

BF1 induced four small molecule transport genes, including MDR1, RTA3, HIP1 and YOR1. MDR1 is a member of the multidrug resistance ("MDR") family belonging to the major facilitator transporter superfamily and has been shown to confer resistance to benomyl, methotrexate, 4-nitroquinoline-N-oxide, cycloheximide, sulfometuron methyl, benztriazoles, and fluconazole in C. albicans. The current data suggest that MDR1 may play a role in the stress response to furanones. RTA3, involved in fatty acid transport, was also previously found to be induced by caspfungin, estradiol, and ketoconazole. The over-expression of the homologous RTA1 gene in S. cerevisiae leads to significant resistance to the strong inhibitor 7-aminocholesterol. The YOR1 sequence in C. albicans shares 48% identities and 66% positives with S. cerevisiae Yor1p, a membrane transporter of the ABC family involved in the resistance to oligomycin, reveromycin, and aureobasidin A. The induction of YOR1 by BF1 suggests that it is also involved in the C. albicans stress response to brominated furanones.

The genes WOR2 and orf19.2693, related to cell cycling, were also induced by BF1. Orf19.2693, like several genes described above, is induced by exposure to nitric oxide and benomyl. In addition, increased transcription of orf19.2693 was found after exposure to fluconazole for multiple generations, which indicates that orf19.2693 could be involved in the cells' adaptation to fluconazole. WOR2, or white-opaque regulator 2, plays a key role in white-opaque switching and opaque state stability. Opaque state is considered to be sensitive to temperature, resistant to the formation of hyphae, and necessary for mating. The finding in this study suggests that WOR2 could also be involved in the stress response.

Table 3 is a summary of the 21 genes were repressed by furanone by at least 1.5-fold following exposure to 3 μg/mL BF1. The largest categories of repressed genes were of unknown functions (33%), followed by cell wall maintenance (24%), transport of small molecules (19%), and other functions (14%).

TABLE 3

| Systematic Name | Standard Name | Induction expression ratio | Functions |
|---|---|---|---|
| Small molecule transport: | | | |
| orf19.4737 | TPO3 | 0.60 | membrane transporter of the MFS-MDR family |
| orf19.5170 | ENA21 | 0.61 | P-type ATPase involved in Na+ efflux |
| orf19.2959.1 | — | 0.64 | conserved hypothetical protein |
| orf19.4337 | ESBP6 | 0.65 | monocarboxylate permease |
| Others | | | |
| orf19.6073 | HMX1 | 0.59 | heme binding protein |
| orf19.742 | ALD6 | 0.33 | mitochondrial aldehyde dehydrogenase |
| orf19.2896 | SOU1 | 0.60 | peroxisomal 2,4-dienoyl-CoA reductase, and sorbitol utilization protein |
| Cell cycling and DNA processing: | | | |
| orf19.3794 | CSR1 | 0.60 | Putative zinc-finger transcription factor involved in zinc homeostasis |
| Cell wall maintenance: | | | |
| orf19.1097 | ALS4 | 0.42 | cell wall protein |
| orf19.5267 | — | 0.56 | hypothetical protein |

TABLE 3-continued

| Systematic Name | Standard Name | Induction expression ratio | Functions |
|---|---|---|---|
| orf19.3066 | ENG1 | 0.57 | endo-1,3-beta-glucanase |
| orf19.7586 | CHT3 | 0.66 | chitinase 3 precursor |
| orf19.3629 | DSE1 | 0.66 | Predicted cell wall protein |
| Unknown function: | | | |
| orf19.6245 | — | 0.67 | hypothetical protein |
| orf19.7502 | — | 0.67 | hypothetical protein |
| orf19.1344 | — | 0.60 | hypothetical protein |
| orf19.6077 | — | 0.51 | conserved hypothetical protein |
| orf19.716 | — | 0.51 | similar to pore-forming bacterial Septicolysin |
| orf19.270 | — | 0.47 | hypothetical protein |
| orf19.5565 | — | 0.43 | homologous to 3-hydroxyisobutyrate dehydrogenase |
| Response to stress: | | | |
| orf19.5193 | FMA1 | 0.61 | Fluconazole and Membrane Associated protein |

Five genes (ALS2, ENG1, CHT3, DSE1 and orf19.5267) related to cell wall maintenance were repressed by BF1. ENG1 and orf19.5267 have previously been found to be down-regulated in response to caspofungin, one of the echinocandins targeting the cell wall. Expression of orf19.5267 is also repressed by ketoconazole. CHT3 is required for chitinase activity and normal cell separation in C. albicans. Its deletion can result in unseparated mother and daughter cells.

At least two of the cell wall maintenance orfs, CHT3 and DSE1, are regulated by ACE2, a transcription factor involved in the regulation of morphogenesis. Depletion of ACE2 has been shown to lead to cell division failure, lose of virulence and a decrease in cell adherence to plastic surfaces. Since an ACE2 null mutation results in great repression of DSE1 and completely abolishes CHT3 expression, it would be interesting to study the response of an ACE2 null mutant when exposed to furanones.

The cell wall maintenance gene ALS2 was previously found to be involved in adhesion between fungal cells, adhesion to host cells, hyphal growth, and biofilm formation. Hence, the repression of ALS2 can potentially inhibit biofilm formation and the development of drug resistance. Interestingly, FMA1, the only down-regulated stress response gene, was previously found to be up-regulated by ciclopirox olamine and to be involved in the clinical development of fluconazole resistance. Its repression could possibly reduce the opportunity for the development of drug resistance. In previous studies, the deletion of CSR1 caused defects in hyphal growth, and severe cell growth defects under zinc-limited conditions. C. albicans virulence is directly correlated with its ability to switch between yeast and hyphal growth; hence, the inhibition of CSR1 by BF1 could possibly repress the virulence of C. albicans.

The genes TOP3, ENA21, ESBP6 and orf19.2959.1, involved in transport of small molecules, were also repressed by BF1. Interestingly, ENA21 was previously found to be induced by flucytosine, amphotericin B, and ketoconazole.

Example 5

To corroborate the microarray results, four genes were checked with RNA dot blotting for their expression levels under the same conditions tested in microarray analysis: orf19.5604 (MDR1), orf19.2175 (CPD1), orf19.2896 (SOU1) and orf19.5565. The total RNA of a control sample without furanone was used to synthesize complementary DNA (cDNA) using OneStep RT-PCR Kit (QIAGEN Inc.) by following the manufacture's protocol. The annealing temperature was optimized based on the primers and was performed at 50° C. for 1 minute in each cycle. The primer sequences are listed in Table 4. The length of the template cDNA was 457 bp, 364 bp, 455 bp and 423 bp for orf19.5604 (MDR1), orf19.2175 (CPD1), orf19.2896 (SOU1) and orf19.5565, respectively.

The DNA probes labeled with Digoxigenin (DIG)-dUTP were then generated using the same primer sets and PCR DIG Probe Synthesis Kit (Roche® Applied Science, Mannheim, Germany) by following the manufacture's protocol except that the annealing temperature was 48° C. for orf19.2175 and orf19.5565, and 51° C. for orf19.2896 and orf19.5604. Total RNA was isolated from cultures treated under the same conditions as in DNA microarray experiments. To conduct dot blotting, each RNA sample was loaded in duplicate (1.5 µg and 0.5 µg respectively) on a blotting membrane (Boehringer Ingelheim®, Ridgefield, Conn.) using a Bio-Dot Microfiltration Apparatus (Bio-Rad®, Richmond, Calif.). The loaded RNA was fixed to the membrane by drying at 80° C. for 2 hours. Then the DIG-labeled DNA probes were denatured (100° C. water bath, 5 minutes) and hybridized to the RNA samples at 50° C. overnight. The membranes were then washed by following the protocol for DIG labeling and detection (Roche Applied Science). To detect the signal, disodium 3-(4-methoxyspiro {1,2-dioxetane-3,2-(5-chloro)tricycle [3.3.1.1.7]decan}-4-yl)phenyl phosphate (Roche Applied Science) was used as a substrate to generate chemiluminescence. The light signal was recorded using Biomax X-ray films from Kodak (Rochester, N.Y.).

The RNA samples used for dot blotting were isolated from independent cultures treated under the same conditions as in microarray experiments (i.e., treatment with 3 µg/mL BF1 as described above). Blotting results of all the four genes are consistent with the microarray data (induced or repressed). For example, gene CPD1 was induced 12.94- and 10-fold in DNA microarray and RNA dot blotting experiments, respectively.

The blotting results indicate that the microarray data are valid and helpful for understanding the effects of brominated furanones on *C. albicans*.

Example 6

To examine whether the brominated furanones inhibit *C. albicans* growth through a mechanism different from the mechanism used by other antifungal agents, the *C. albicans* gene expression pattern following exposure to BF1 was compared to gene expression patterns following exposure to other antifungal agents. Table 5 is a summary of the genes that are induced by both BF1 and antifungal agents nitric oxide, azole, caspofungin, and amphotericin B, with the following exceptions: (i) the starred genes—orf19.1344, ENA21, and FMA1—are repressed by BF1 but confer azole resistance; and (ii) the genes in bold—ENG1 and orf19.5267—are repressed by both BF1 and caspofungin.

TABLE 4

| Antifungal compounds | Benomyl | Nitric oxide | Azole | Caspofungin | Amphotericin B |
|---|---|---|---|---|---|
| Genes Induced by both BF1 and these antifungal agents | MDR1 TTR2 IFR2 OYE23 OYE32 EBP1 orf19.3139 orf19.7531 orf19.7306 orf19.2262 | YHB1 OYE23 EBP1 OYE32 OYE2 orf19.2693 orf19.2262 orf19.2175 | MDR1 orf19.7306 orf19.2694 Orf19.1344* ENA21 * FMA1* | RTA3 orf19.7531 ENG1 orf19.5267 | SOD2 OYE32 |

Among the genes affected by BF1, ten of them overlapped with those affected by benomyl, one of the benzimidazole fungicides, as shown in Table 4. Eight genes affected by BF1 were also induced by nitric oxide. As for the antifungal drugs currently available, four genes overlapped with the azole-class drug-induced genes and only two genes were induced by both BF1 and amphotericin B, or by caspofungin. Among all of the 21 repressed genes, two (ENG1 and orf19.5267) overlapped with genes down-regulated by caspofungin. Interestingly, orf19.1344, ENA21 and FMA1 were found to be related to azole resistance, and orf19.6245 was previously found to be up-regulated under oxidative stress ($H_2O_2$).

The difference in gene expression patterns between treatment by furanones and other antifungal compounds suggests that BF1 inhibits *C. albicans* growth through an alternative mechanism with different cellular targets. Thus, brominated furanones may be effective in controlling fungal pathogens that are resistant to other antifungal agents. Although the exact mechanism of inhibition by BFs remains unknown, the induction of oxidative stress response genes and the repression of cell wall maintenance genes suggest that BF1 could possibly cause the intracellular generation of high-level reactive oxygen species and consequent cell death. On the other hand, BFs could potentially damage the cell wall by inhibiting the genes involved in cell wall maintenance and lead to cell lysis.

Example 7

Research has shown that brominated furanones, produced as secondary metabolites by the marine red macro alga *Delisea pulchra*, have strong antifouling activities and are able to inhibit bacterial biofilm formation and quorum sensing ("QS") (i.e., cell-to-cell communication to monitor population density and regulate gene expression) in Gram-negative bacteria. Biofilms are sessile microbial communities formed on surfaces. These multicellular structures cause serious problems of infections in humans and biofouling in industrial settings. Due to the high resistance of bacterial biofilms to antibiotics and disinfectants, biofilm cells can survive treatments and serve as a nidus for seeding microbes and release of extracellular toxins, presenting a great challenge to treatment. It is well documented that bacteria use small signaling molecules for cell-cell communication, a system known as quorum sensing (QS), that controls the expression of virulence factors and biofilm formation. Thus, inhibiting quorum sensing is a promising target for effective control of biofilm infections.

In this Example, nine furanones—including seven brominated furanones (BF8, BF9, BF10, BF11, BF12, BF13, and BF14) and two nonbrominated furanones (NF1 and NF3)—with systematic changes in their structures were tested for their ability to inhibit the planktonic growth of *Pseudomonas aeruginosa* ("*P. aeruginosa*"). The systematic changes in the structure allow the differential effects of the furanones on microbial growth to be rigorously correlated with their structures.

The antimicrobial activities of furanones on the planktonic growth of *P. aeruginosa* strain PAO1 was examined using a microplate based growth assay. An overnight culture of the strain grown in LB medium at 30° C. was used to inoculate M63 minimal medium supplemented with furanones at 0, 30 or 60 μg/mL to an optical density at 600 nm (OD600) of 0.05 in 96-well plates. The plates were then incubated at 30° C. with shaking at 200 rpm. The reading of $OD_{600}$ was measured every 60 minutes for six hours using a microplate reader (ELx808, BioTek Instruments). Six replicates were tested for every sample. The synthesis of the brominated furanones, the structures of which are shown in FIGS. 1A and 1B, was according to Example 1.

Figure 7A:
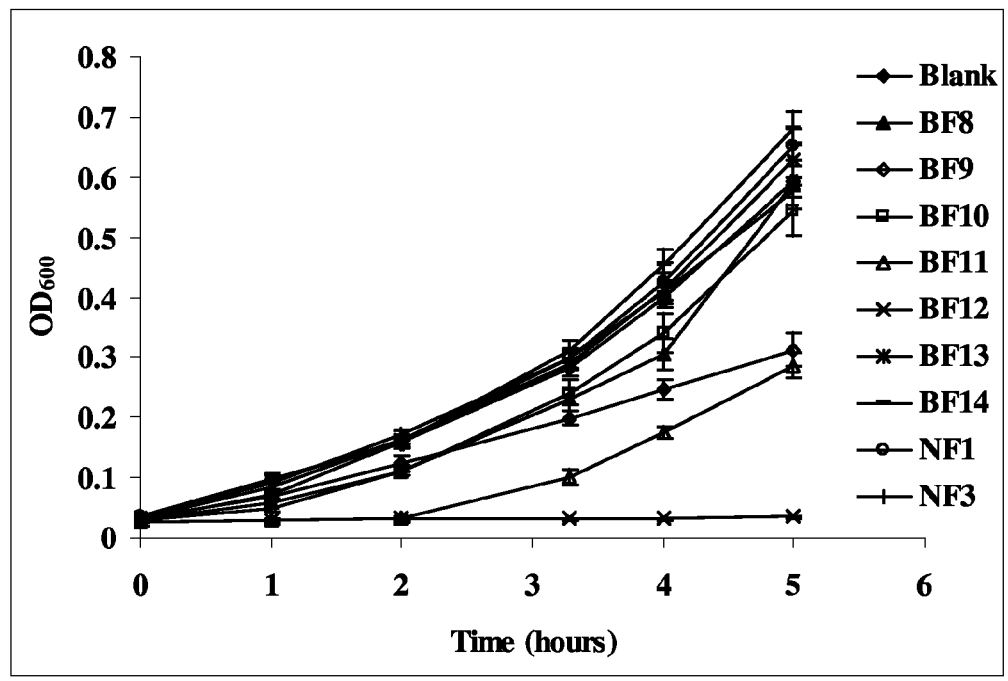
FIG. 7A is a graph of the antimicrobial effects of 30 µg/mL of furanone on the planktonic growth of *Pseudomonas aeruginosa*.
Figure 7B:
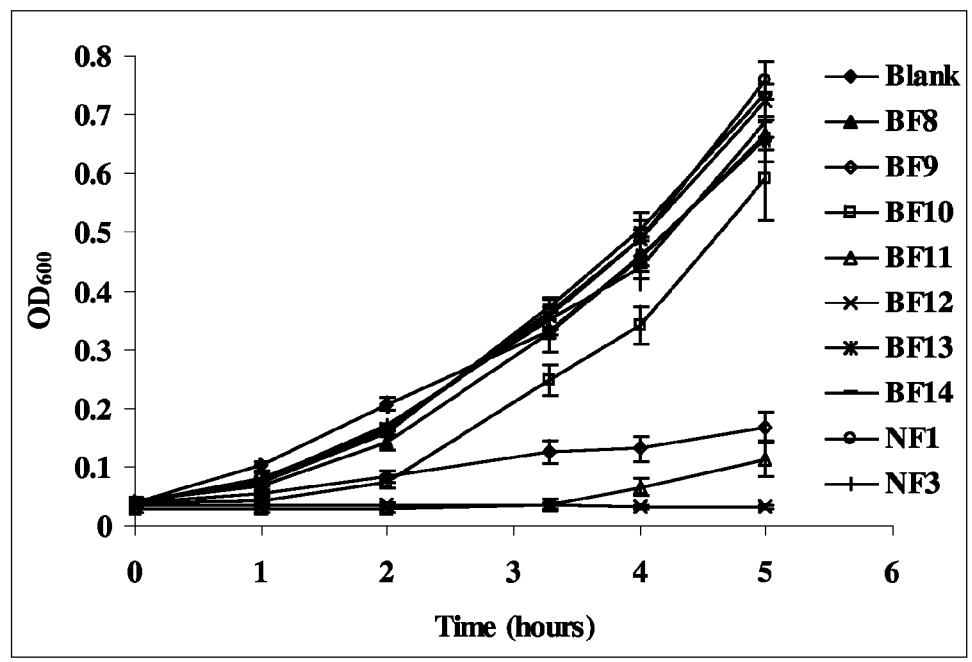
FIG. 7B is a graph of the antimicrobial effects of 60 µg/mL of furanone on the planktonic growth of *Pseudomonas aeruginosa*.

FIG. 7A is a graph of the growth curve of *P. aeruginosa* strain PAO1 exposed to 30 μg/mL of furanone, and FIG. 7B is a graph of the growth curve of the same strain exposed to 60 μg/mL of furanone. At 30 μg/mL, BF9, BF11 and BF12 reduced the specific growth rates by 29.3%, 27.3% and 91.2%, respectively, compared to that of furanone-free control, while BF8, BF10, BF13, BF14, NF1 and NF3 did not exhibit significant inhibitory effects. At 60 μg/mL, BF9, BF11 and BF12 reduced the specific growth rates by 42.7%, 65.0% and 100%, respectively. Interestingly, at 60 μg/mL, BF10 extended the lag phase by one hour, but the specific growth rate was only reduced by 10%. NFs did not show any significant inhibitory effect on planktonic growth, which suggests that bromine group is necessary to the inhibition. Considering the strong toxicity of BF11 and BF12 to *E. coli* (not shown) and *Candida albicans*, these findings suggest that monosubstituted bromides on an exocyclic methyl group (bromomethyl, —$CH_2$—Br) lead to high toxicity to both bacteria and fungi. In comparison, although BF9 does not inhibit the growth of *E. coli* up to 60 μg/mL (data not shown), it significantly inhibited the growth of *P. aeruginosa* strain PAO1 at 30 μg/mL. Although BF8 did not inhibit the growth of *E. coli* and *P. aeruginosa* at up to 60 μg/mL, it was able to inhibit the growth of *C. albicans* at 5 μg/mL. These results indicate that furanones may have multiple targets in different microbial species, which may lower the risk of potential development of resistance in microbes.

Additionally, since BF9, BF11, and BF12 at both 30 μg/mL and 60 μg/mL showed significant inhibition of planktonic growth with a potency in the order of BF12>BF11>BF9, the results suggest that the exocyclic bromomethyl group leads to high toxicity to *P. aeruginosa*, which is consistent with the previous report for *E. coli*.

Example 8

In this Example, nine furanones—including seven brominated furanones (BF8, BF9, BF10, BF11, BF12, BF13, and BF14) and two nonbrominated furanones (NF1 and NF3)—with systematic changes in their structures were tested for their ability to inhibit the biofilm formation of *P. aeruginosa*.

A microplate-based biofilm assay was used to further investigate whether furanones inhibit biofilm formation of *P. aeruginosa* strain PAO1. For this biofilm assay the strain was grown at 30° C. without shaking in M63 minimal medium containing 13.6 g/L $KH_2PO_4$, 2 g/L $(NH_4)_2SO_4$, 0.5 mg/L $FeSO_4$, 0.12 g/L $MgSO_4$, 5 g/L vitamin free casamino acids and 5 g/L glucose (pH 7.0). The synthesis of the brominated furanones, the structures of which are shown in FIGS. 1A and 1B, was according to Example 1.

The overnight culture of *P. aeruginosa* was used to inoculate fresh M63 medium supplemented with furanones (0, 30 or 60 μg/mL) to an $OD_{600}$ of 0.05 in 96-well plates. Four replicates were tested for each condition. The plates were incubated at 30° C. without shaking for 24 hours. The biofilm mass was quantified by following the protocol described previously. Briefly, the planktonic cells were carefully removed by pipetting and the plates with biofilms were washed three times with deionized $H_2O$ and dried by gently patting on a piece of paper towel. To quantify biofilms, the plates were stained with 0.1% crystal violet and incubated for 20 minutes at room temperature. The plates were then washed three times with deionized $H_2O$ to remove extra dyes. An $OD_{540}$ was measured to quantify the biofilm on the bottom of each well.

Figure 8A:
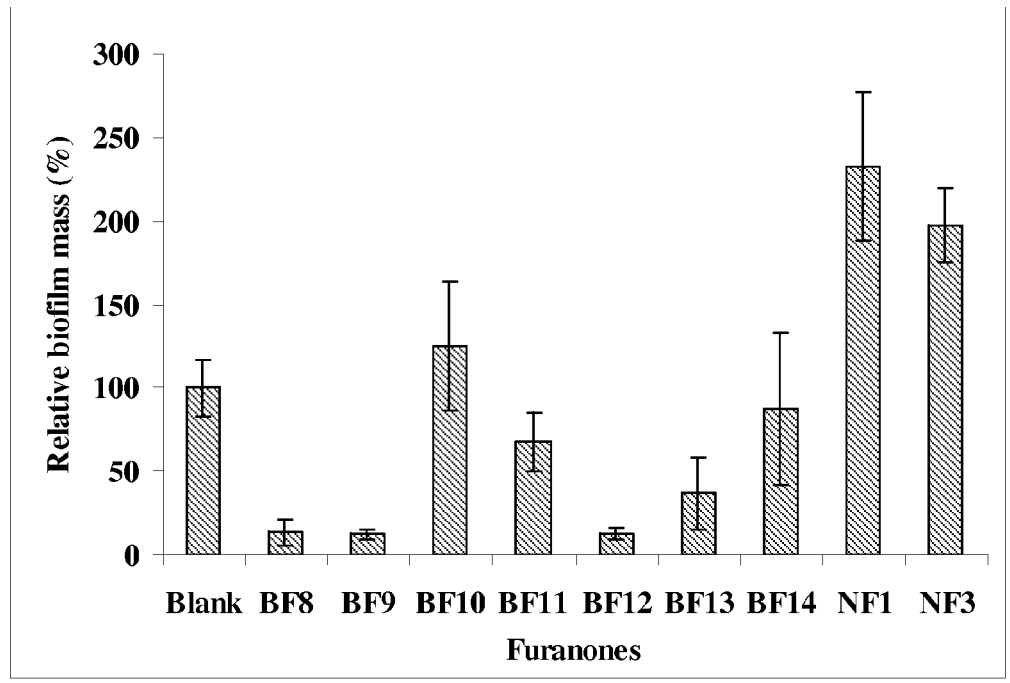
FIG. 8A is a graph of the antimicrobial effects of 30 µg/mL of furanone on the biofilm formation of *Pseudomonas aeruginosa*.
Figure 8B:
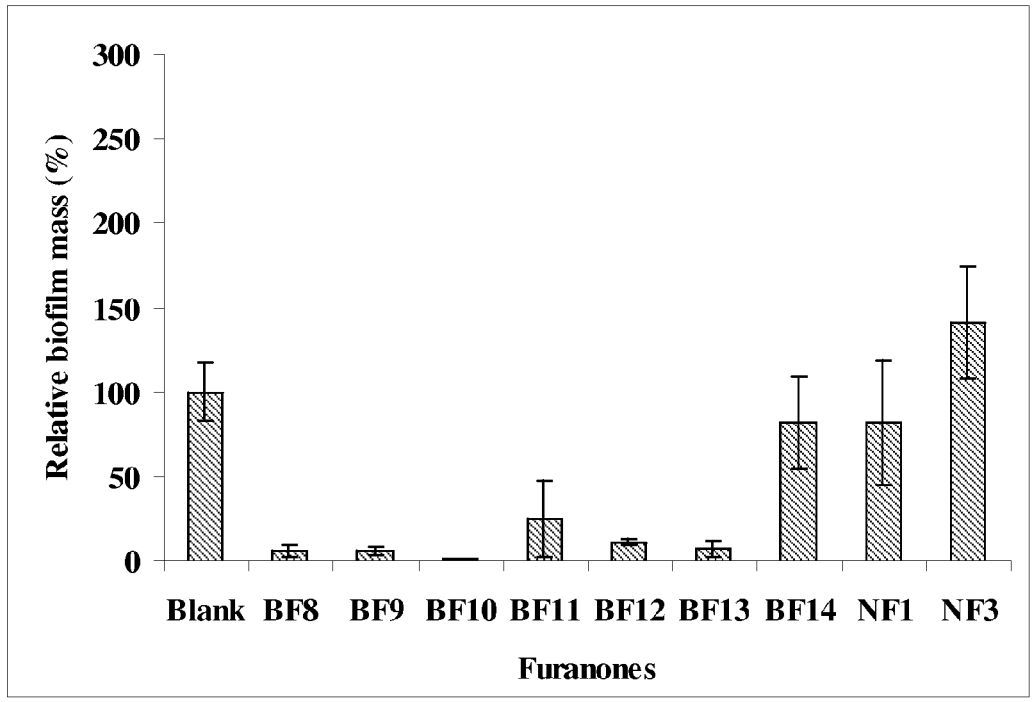
FIG. 8B is a graph of the antimicrobial effects of 60 µg/mL of furanone on the biofilm formation of *Pseudomonas aeruginosa*.

FIG. 8A is a graph showing the effects of 30 μg/mL of BFs or NFs on biofilm formation of *P. aeruginosa* strain PAO1, and FIG. 8B is a graph showing the effects of 60 μg/mL of BFs or NFs on biofilm formation by the strain. In each figure, the relative biofilm mass (%) in the presence of furanones at 30 μg/mL and 60 μg/mL was normalized by that of furanone-free control. As FIGS. 8A and 8B show, biofilm formation was significantly inhibited by BF8, BF9, BF11, BF12 and BF13 at 30 μg/mL and 60 μg/mL, as well as by BF10 at 60 μg/mL, when compared to furanone-free control.

Although BF8 had no apparent effect on planktonic growth at these concentrations, it showed inhibition of biofilm formation by 86.1±7.6% and 93.8±3.7% at 30 and 60 μg/mL, respectively, when compared to the 24-hour biofilm mass of furanone-free control. This result is consistent with the previous finding that BFs can inhibit the biofilm formation of *E. coli* at concentrations non-inhibitory to its growth. Biofilm inhibition by BF9, BF11 and BF12 is consistent with their inhibitory effects on the planktonic growth of *P. aeruginosa* PAO1 as shown in FIG. 7A and FIG. 7B. Interestingly, while BF10 at 30 μg/mL didn't show apparent inhibition of biofilm formation, it inhibited biofilm formation completely at 60 μg/mL, suggesting that a threshold concentration may exist for its inhibition.

The nonbrominated furanones did not show any inhibitory effect, which indicates that bromine is necessary to biofilm inhibition. The inhibitory BFs bear either an exocyclic vinyl bromide (=CH—Br) group (BF8 and BF12) or an exocyclic vinylidene bromide (=C—Br2) group (BF9, BF10, and BF11), while non-inhibitory BF (BF14) does not contain these components. This finding suggests that the exocyclic vinyl bromide and vinylidene bromide conjugated with the carbonyl group are important structural elements for biofilm inhibition.

Biofilms are well known to be extremely tolerant to antibiotics and disinfectants. However, it was found that the concentrations of these furanones required to inhibit biofilm formation were similar to those for inhibiting planktonic cell growth in this study. It will be important to further explore the effects of furanones on the mature biofilms of *P. aeruginosa*.

Example 9

To explore if brominated furanones have an interaction with quorum-sensing based on AI-2, a bioluminescence assay was conducted. Specifically, to examine whether the novel BFs have any inhibitory effects on universal QS signal AI-2, the bioluminescence of the reporter *Vibrio harveyi* ("*V. harveyi*") strain BB170 was used as an indicator of AI-2 activities.

The *E. coli* strains RP437 [thr-1(Am) leuB6 his-4 metF159 (Am) eda-50 rpsL1356 thi-1 ara-14 mtl-1 xyl-5 tonA31 tsx-78 lacY1 F-] and quorum-sensing mutant BW25113 ΔLuxS [ΔluxS::kan$^r$ lacI$^q$ rrnB3 ΔlacZ4787 hsdR514 Δ(araBAD)567 Δ (rhaBAD)568 rph-1] were routinely grown at 37° C. with shaking at 200 rpm in LB medium containing 10 g/L NaCl, 5 g/L yeast extract and 10 g/L tryptone. The AI-2 reporter strain *V. harveyi* BB170 [BB120 luxN::Tn5 (AI-1 sensor-, AI-2 sensor-0] was obtained from the American Type Culture Collection (ATCC, Manassas, Va.) and grown at 30° C. with shaking at 200 rpm in AB medium containing 17.5 g/L NaCl, 6 g/L MgSO4 and 2 g/L vitamin-free casamino acid. The synthesis of the brominated furanones (BF8-BF10) was as described in Example 1, and the structures are shown in FIGS. 1A and 1B.

The bioluminescence assay was conducted using an assay known to those skilled in the art. Specifically, the overnight culture of *E. coli* RP437 (AI-2 positive) and *E. coli* BW25113 ΔLuxS (AI-2 negative) grown in LB medium were used to inoculate subcultures by 1:100 dilution in LB medium supplemented with 5 g/L glucose as well as 60 μg/mL of BF8, BF9 or BF10. Furanone-free cultures were also included as negative controls. The amounts of ethanol and methanol were adjusted to be the same for all the samples in order to eliminate the effects of solvents. The samples were incubated at 37° C. for 8 hours and then the supernatants were obtained by centrifugation at 4° C. and 13,200 rpm for 10 minutes (Model 5415D, Ependorf North America Inc., Westbury, N.Y.). The supernatants were sterilized by passing through 0.2 μm filters and stored at −20° C. till use.

The reporter strain *V. harveyi* BB170 was grown in AB medium at 30° C. for 16 hours. The overnight culture was used to inoculate the subcultures by 1:5000 dilutions in fresh AB medium with the above supernatants added to a concentration of 10% (v/v). The subcultures were incubated at 30° C. and the bioluminescence was measured every hour as an indicator of AI-2 activity using a luminometer (Model 20/20m Turner BioSystems, Inc., Sunnyvale, Calif.). The colony-forming units (CFUs) of *V. harveyi* strain BB170 were counted after spreading the cell cultures on LM agar plates containing 10 g/L tryptone, 5 g/L yeast extract, 20 g/L NaCl and 15 g/L agar plates and incubating at 30° C. for 24 hours.

Figure 9:
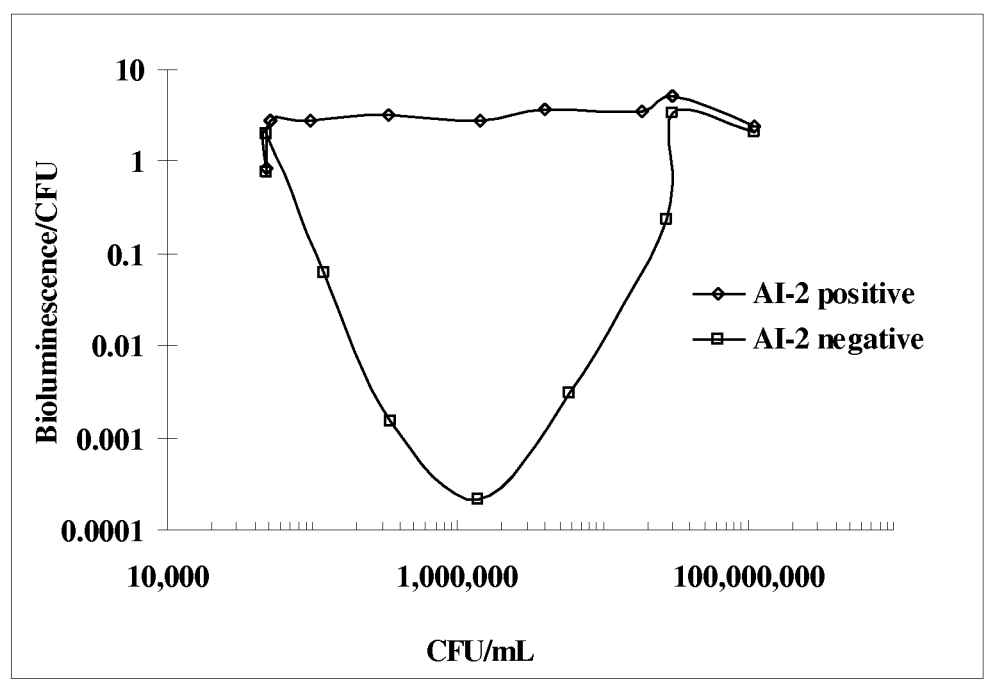
FIG. 9 is a graph of the relative bioluminescence (bioluminescence/CFU) of *V. harveyi* strain BB170 in the presence and absence of AI-2.

It was previously known that the *V. harveyi* BB170 strain produces luminescence in response to AI-2 but not in response to homoserine lactones (AHLs) as a result of a mutation in the AHL sensor gene. At low cell densities, the basal level of AI-2 will not trigger significant production of luminescence in *V. harveyi* BB170; however, at high cell densities, the extracellular AI-2 concentration will reach a certain threshold and induce the bioluminescence of *V. harveyi*. Therefore, with the addition of *E. coli* supernatant containing AI-2, the bioluminescence will be induced at very low cell densities. Thus, by adding furanones to the *E. coli* cultures and test their AI-2 activities, it is possible to evaluate the QS inhibition by furanones. FIG. 9 is a graph showing the relative bioluminescence (bioluminescence/CFU) of *V. harveyi* strain BB170 in the presence and absence of AI-2. The maximum difference in relative bioluminescence between the two conditions indicates the relative AI-2 activity.

Figure 10:
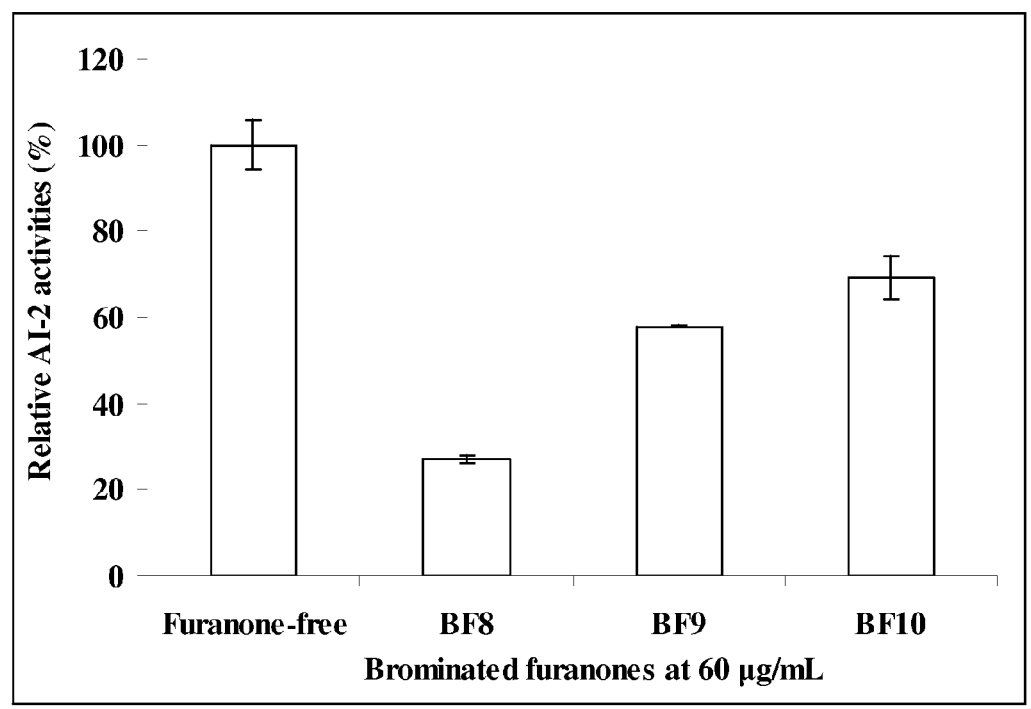
FIG. 10 is a graph of the extracellular AI-2 activities of *E. coli* following exposure to 60 µg/mL of furanones.

FIG. 10 is a graph of the extracellular AI-2 activities of *E. coli* following exposure to 60 μg/mL of furanones. Compared to the supernatants of *E. coli* cultures grown without BFs, the supernatants harvested from *E. coli* culture grown with 60 μg/mL BF8, BF9 or BF10 had significantly lower AI-2 activities. That is, there were 72.9±1.0%, 42.2±0.3%, and 31.0±5.1% reductions by BF8, BF9 and BF10, respectively, as shown in FIG. 10. Comparing the chemical structures of BF8, BF9 and BF10, it was found that BF8 contains a exocyclic vinyl bromide group (=CH—Br), while BF9 and BF10 contain a exocyclic vinylidene bromide group (=C—Br2). This finding suggests that exocyclic vinyl bromide group in BF8 is important for the inhibition of AI-2 QS by furanones. Compared to BF9, BF10 contains a exocyclic dibromomethyl group (—CH—Br$_2$) rather than exocyclic methyl group (—CH$_3$), which is the only structural difference between them. Since these two BFs had similar inhibition of extracellular AI-2 activities, this exocyclic dibromomethyl group may not be important to the inhibitory activity on AI-2 QS.

In conclusion, the discovery of key structural elements in this Example provides important information for the development of potent antagonists to control bacterial multicellular behaviors including biofilm formation and quorum sensing. The BFs that can inhibit biofilm formation at relatively low concentrations may have both clinical and industrial applications.

Example 10

This Example examines the effect of brominated furanones on the growth of fungi associated with damage to building material. Six fungal strains were the subject of these experiments; *Gloeophyllum trabeum* (strains GT598 and GT599), *Chaetomium globosum* (wildtype strain and CG572), and *Trametes versicolor* (strains TV7B2-59 and TV57MAD277). The species were developed on 2% Malt-Extract Agar (MEA) plates and stored inverted at 4° C. The stocks were refreshed by streaking new plates every two months.

The brominated and non-brominated furanones were added to MAE agar plates at different concentrations. The brominated furanones were dissolved in either ethanol ("EtOH") or methanol ("MeOH") as stock solutions, as shown in Table 5. The non-brominated furanones were purchased from Sigma (St. Louis, Mo.). The furanone stocks were stored at 4° C.

TABLE 5

| Furanone | Solvent | Stock Concentration |
|---|---|---|
| BF1 | EtOH | 30 mg/mL |
| BF8 | EtOH | 30 mg/mL |
| BF9 | EtOH | 20 mg/mL |
| BF10 | MeOH | 20 mg/mL |
| BF11 | EtOH | 20 mg/mL |
| BF12 | EtOH | 20 mg/mL |
| BF13 | EtOH | 20 mg/mL |
| BF15 | EtOH | 20 mg/mL |
| NF1 | EtOH | 20 mg/mL |
| NF2 | EtOH | 20 mg/mL |

MAE agar plates containing the same amounts of ethanol/methanol were also prepared as negative controls to eliminate any solvent effects. The plates were prepared using either 90 mm or 60 mm petri dishes and were stored inverted at 4° C. until use.

Different concentrations of furanones were studied to compare their antifungal activities. The plates were inoculated with the six fungal strains using a platinum loop and were incubated upside down at 30° C. for 7 days to monitor the growth. The initial screening was performed using a single 60 μg/mL furanone concentration. Furanones that exhibited inhibitory activities were further studied at lower concentrations of 1, 5, or 30 μg/mL.

As show in Table 6, at an initial concentration of 60 μg/mL each of the brominated furanones were found to inhibit the growth of all the six fungal species tested.

TABLE 6

| Furanone | GT598 | GT599 | CG | CG572 | TV7B2-59 | TV57MAD277 |
|---|---|---|---|---|---|---|
| (−) control | − | − | − | − | − | − |
| (+) control | + | + | + | + | + | + |
| BF1 | − | − | − | − | − | − |
| BF8 | − | − | − | − | − | − |
| BF9 | − | − | − | − | − | − |
| BF10 | − | − | − | − | − | − |
| BF11 | − | − | − | − | − | − |
| BF15 | − | − | − | − | − | − |

No growth was observed on the plates containing brominated furanones after 7 days of incubation, while normal growth was seen on all the control plates without furanone. In comparison, the non-brominated furanone NF2 did not show any apparent inhibition, suggesting that presence of the Br atom might be essential. Since each of the brominated furanones were inhibitory at 60 µg/mL, further tests with lower concentrations were conducted to compare the activities of different furanones. Initially, the brominated furanones were tested at 5 µg/mL. The compounds that inhibited growth at 5 µg/mL were then tested at a concentration of 1 µg/mL. The compounds that exhibited growth at 5 µg/mL were tested at 30 µg/mL. Table 7 shows the results of the growth inhibition tests, with concentrations ranging from 1 to 60 µg/mL.

TABLE 7

| Furanone | GT598 | GT599 | CG | CG572 | TV7B2-59 | TV57MAD277 |
|---|---|---|---|---|---|---|
| BF1 | 30 | 30 | 30 | 30 | 5 | 5 |
| BF8 | 5 | 5 | 5 | 30 | 30 | 30 |
| BF9 | 60 | 60 | 5 | 60 | 5 | 5 |
| BF10 | 30 | 30 | 30 | 30 | 30 | 5 |
| BF11 | 1 | 5 | 5 | 5 | 5 | 5 |
| BF12 | 1 | 5 | 1 | 5 | 5 | 5 |
| BF13 | 60 | 60 | 60 | 60 | 60 | 5 |
| NF1 | 60 | 60 | 60 | 60 | 60 | 60 |
| NF2 | N/A | N/A | N/A | N/A | N/A | N/A |

As shown in Table 7, the most significant inhibition occurred with synthetic furanones BF11 and BF12. The common component of furanones BF11 and BF12 is a bromine group off of a carbon group at C-2 of the aromatic structure. Natural furanone, also referred to as furanone BF1, was also effective at preventing growth in low concentrations.

The results suggest that brominated furanones can be used as a wood preservative. Advantages of using furanones include reduced environmental impact due to the use of a naturally occurring or derivative, innocuous agent and since wood would not need to be impregnated with furanone under extreme heat or pressure, the structural strength would not be altered. Any method of wood preservation known to those in the art may be used for wood treatment using brominated furanones, including but not limited to soaking the wood in brominated furanones before use, using furanones in conjunction with vacuum or pressure methods to treat the wood before use, spraying the wood with brominated furanones before use, or applying furanones to the wood after material has already been incorporated into a structure. It could also include painting or staining the wood with material containing brominated furanones.

Brominated furanones can be utilized in a number of different ways to prevent the growth of microorganisms or treat microorganism infection. An aerosol delivery mechanism, for example, can be used to deliver aerosolized BFs to areas of microorganism growth on or in the human body. This includes a simple spray bottle design used to treat or prevent microorganism infections in the throat or mouth.

Brominated furanones can also be used as a topical agent to treat surface infections. Many of the prior art formulations used to treat *Candida albicans* infection, for example, are used as topical agents. Sublethal doses of BFs can be delivered intravenously as a preventative measure or as a method to treat microorganism infections.

To prevent microorganism growth associated with wound dressings, the dressings can be soaked in or otherwise treated with brominated furanones. This may be especially useful for dressings that are prone to microorganism growth.

Brominated furanones can also be utilized to prevent biofilm formation on medical devices by soaking the devices in the furanones or otherwise treating the devices with brominated furanones. These medical devices can include intravenous catheters, joint prostheses, cardiac pacemakers, prosthetic heart valves, peritoneal dialysis catheters and cerebrospinal fluid shunts, among many others. For prolonged protection against the growth of microorganisms and biofilm formation, the devices can contain a time-release mechanism to slowly release active amounts of brominated furanones onto the surface of the device or into surrounding tissue.

For example, U.S. patent application Ser. No. 12/233,337, hereby incorporated by reference in its entirety, discloses a water-in-water emulsion system for delivery of brominated furnones, including the brominated furanones of the present invention. It should be recognized by those of skill in the art that other, known delivery mechanisms for applying antimicrobial agents to various objects and as treatments for humans, both external and internal, may be utilized I combination with the brominated furanones of the present invention.

Although the present invention has been described in connection with various embodiments, it should be understood that modifications, alterations, and additions can be made to the invention without departing from the scope of the invention as defined by the claims.

What is claimed is:

1. A brominated furanone having a structure selected from the group consisting of:

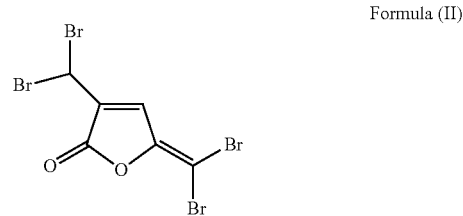 [SMILES: O=C1OC(=C(Br)Br)C=C1C(Br)Br]

Formula (II)

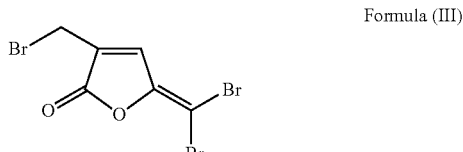

Formula (III)

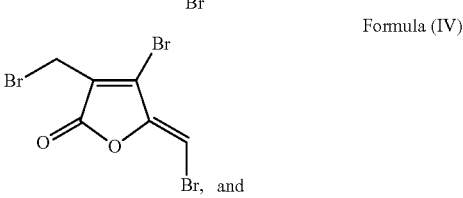

Formula (IV)

Br, and

-continued
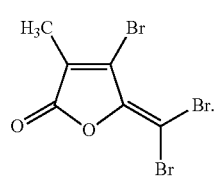
Formula (V)
2. The brominated furanone of claim 1, wherein the structure comprises:
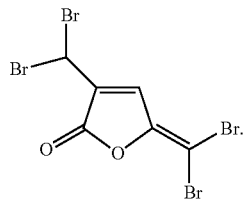
Formula (II)
3. The brominated furanone of claim 1, wherein the structure comprises:
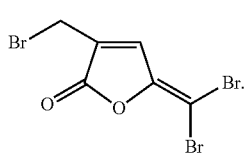
Formula (III)
4. The brominated furanone of claim 1, wherein the structure comprises:
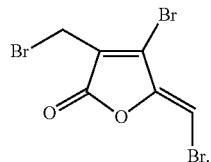
Formula (IV)
5. The brominated furanone of claim 1, wherein the structure comprises:
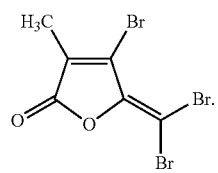
Formula (V)
* * * * *